(12) United States Patent
Okada et al.

(10) Patent No.: US 11,312,928 B2
(45) Date of Patent: Apr. 26, 2022

(54) DETERGENT COMPOSITION COMPRISING AN ACIDIC SOPHOROSE LIPID AND FATTY ACID SALT MIXTURE

(71) Applicant: SARAYA CO., LTD., Osaka (JP)

(72) Inventors: Emi Okada, Kashiwara (JP); Reiko Matsumura, Kashiwara (JP); Masashi Yamamoto, Kashiwara (JP)

(73) Assignee: SARAYA CO., LTD., Osaka (JP)

( * ) Notice: Subject to any disclaimer, the term of this patent is extended or adjusted under 35 U.S.C. 154(b) by 132 days.

(21) Appl. No.: 16/491,511

(22) PCT Filed: Mar. 7, 2018

(86) PCT No.: PCT/JP2018/008865
§ 371 (c)(1),
(2) Date: Sep. 5, 2019

(87) PCT Pub. No.: WO2018/164204
PCT Pub. Date: Sep. 13, 2018

(65) Prior Publication Data
US 2020/0032168 A1 Jan. 30, 2020

(30) Foreign Application Priority Data

Mar. 7, 2017 (JP) .............................. JP2017-043340
Nov. 15, 2017 (WO) .................. PCT/JP2017/041133

(51) Int. Cl.
| | |
|---|---|
| C11D 1/04 | (2006.01) |
| C11D 3/38 | (2006.01) |
| A61K 8/04 | (2006.01) |
| A61K 8/36 | (2006.01) |
| A61K 8/99 | (2017.01) |
| A61Q 5/02 | (2006.01) |
| A61Q 19/10 | (2006.01) |
| C11D 1/66 | (2006.01) |
| C11D 17/00 | (2006.01) |

(52) U.S. Cl.
CPC ................ *C11D 3/38* (2013.01); *A61K 8/046* (2013.01); *A61K 8/361* (2013.01); *A61K 8/99* (2013.01); *A61Q 5/02* (2013.01); *A61Q 19/10* (2013.01); *C11D 1/667* (2013.01); *C11D 17/0043* (2013.01); *A61K 2800/85* (2013.01)

(58) Field of Classification Search
CPC ..... C11D 1/04; C11D 3/2079; C11D 11/0023; C11D 17/08; C11D 17/0047
See application file for complete search history.

(56) References Cited

U.S. PATENT DOCUMENTS

| | | | |
|---|---|---|---|
| 5,417,879 A | 5/1995 | Hall et al. | |
| 5,688,930 A * | 11/1997 | Bertho | C11D 1/662 536/18.6 |
| 5,756,471 A | 5/1998 | Hillion et al. | |
| 5,981,497 A | 11/1999 | Maingault | |
| 6,057,302 A | 5/2000 | Borzeix | |
| 10,065,982 B2 | 9/2018 | Hirata et al. | |
| 10,688,031 B2 | 6/2020 | Ito et al. | |
| 10,752,650 B2 | 8/2020 | Araki et al. | |
| 2004/0171512 A1 | 9/2004 | Furuta et al. | |
| 2011/0237531 A1 | 9/2011 | Yanagisawa et al. | |
| 2012/0142621 A1 | 6/2012 | Falus et al. | |
| 2012/0220464 A1 | 8/2012 | Giessler-Blank et al. | |
| 2013/0035403 A1 | 2/2013 | Schaffer et al. | |
| 2014/0349902 A1* | 11/2014 | Allef | A61K 8/361 510/119 |
| 2015/0112049 A1 | 4/2015 | Hirata et al. | |
| 2015/0203443 A1* | 7/2015 | Klostermann | C11D 17/003 424/94.1 |
| 2016/0280733 A1 | 9/2016 | Araki et al. | |

(Continued)

FOREIGN PATENT DOCUMENTS

| | | |
|---|---|---|
| CN | 104968325 A | 10/2015 |
| EP | 0499434 A1 | 8/1992 |

(Continued)

OTHER PUBLICATIONS

China National Intellectual Property Administration, First Office Action in Chinese Patent Application No. 201880016429.6 (Oct. 19, 2020).
[ No Author Listed ] ALTERN. Animal Test. Experiment, Guideline Draft, 5(Supplement): 1-3 (1998).
Ashby et al., "Property control of sophorolipids: influence of fatty acid substrate and blending," *Biotechnol. Lett.* 30(6): 1093-1100 (2008).
Asmer et al., "Microbial production , structure elucidation and bioconversion of sophorose lipids," *J. American Oil Chem. Soc.*, 65(9): 1460-1466 (1988).
Brakemeier et al., *Candida bombicola*: production of novel alkyl glycosides based on glucose/2-dodecanol, *Appl. Microbiol. Biotechnol.*, 50(2): 161-166 (1998).

(Continued)

*Primary Examiner* — Charles I Boyer
(74) *Attorney, Agent, or Firm* — Leydig, Voit & Mayer, Ltd.

(57) ABSTRACT

This invention provides a cleaning agent composition that exhibits good storage stability, especially storage stability at low temperature, and a cleaning agent composition that can be favorably dispensed from a dispenser. The cleaning agent composition of the present invention comprises (a) a fatty acid salt and (b) a sophorose lipid, wherein the proportion of the component (a) is 4 to 18 mass % based on the cleaning agent composition taken as 100 mass %; the proportion of a fatty acid salt having 12 or fewer carbon atoms is 15 parts by mass or more, and the proportion of a fatty acid salt having 16 or more carbon atoms is 60 parts by mass or less, based on 100 parts by mass of the total amount of the component (a); the proportion of an acidic sophorose lipid is 80 mass % or more based on the total amount of the component (b) taken as 100 mass %; and the proportion of the component (b) is 5 to 80 parts by mass per 100 parts by mass of the total amount of the component (a).

15 Claims, No Drawings

(56) References Cited

U.S. PATENT DOCUMENTS

| | | | | |
|---|---|---|---|---|
| 2016/0324747 | A1* | 11/2016 | Ito | A61K 31/27 |
| 2018/0256489 | A1* | 9/2018 | Silberstein | A61K 8/73 |

FOREIGN PATENT DOCUMENTS

| | | | |
|---|---|---|---|
| EP | 2351847 | A1 | 8/2011 |
| JP | S56-022399 | A | 3/1981 |
| JP | H04-170499 | A | 6/1992 |
| JP | H05-059394 | A | 3/1993 |
| JP | H07-118284 | A | 5/1995 |
| JP | H10-501260 | A | 2/1998 |
| JP | H11-508549 | A | 7/1999 |
| JP | 2002-045195 | A | 2/2002 |
| JP | 2003-009896 | A | 1/2003 |
| JP | 2003-013093 | A | 1/2003 |
| JP | 2006-070231 | A | 3/2006 |
| JP | 2006-083238 | A | 3/2006 |
| JP | 2006083238 | * | 3/2006 |
| JP | 2006-212086 | A | 8/2006 |
| JP | 2008-247845 | A | 10/2008 |
| JP | 2009-062288 | A | 3/2009 |
| JP | 2009-531310 | A | 9/2009 |
| JP | 2009-275145 | A | 11/2009 |
| JP | 2009275145 | * | 11/2009 |
| JP | 2013-511266 | A | 4/2013 |
| JP | 2014-117240 | A | 6/2014 |
| JP | 2014-150774 | A | 8/2014 |
| JP | 2016-160244 | A | 9/2016 |
| WO | WO 2007/130738 | A1 | 11/2007 |
| WO | WO 2010/050413 | A1 | 5/2010 |
| WO | WO 2011/061032 | A2 | 5/2011 |
| WO | WO 2011/127101 | A1 | 10/2011 |
| WO | WO 2013/129667 | A1 | 9/2013 |
| WO | WO 2015/034007 | A1 | 3/2015 |

OTHER PUBLICATIONS

Cavalero et al., "The effect of medium composition on the structure and physical state of sophorolipids produced by Candida bombicola ATCC 22214," J. Biotech., 103(1): 31-41 (2003).

Cooper et al., "Production of a Biosurfactant from Torulopsis bombicola," Appl. Environ. Microbiol., 47(1): 173-176 (1984).

Daniel et al., "Sophorolipid Production with High Yields on Whey Concentrate and Rapeseed Oil without Consumption of Lactose," Biotech. Lett., 20(8): 805-807 (1998).

Daverey, "Production, Characterization, and Properties of Sophorolipids from the Yeast Candida bombicola using a Low-cost Fermentative Medium " Appl. Biochem. Biotechnol., 158(3): 663-674 (2009).

Davila et al., "Kinetics and balance of a fermentation free from product inhibition: sophorose lipid production by Candida bombicola," Appl. Microbil. Biotechnol., 38: 6-11 (1992).

Davila et al., "Identification and determination of individual sophorolipids in fermentation products by gradient elution high performance liquid chromatography with evaporative light-scattering detection," J. Chromatogr., 648(1): 139-149 (1993).

Deshpande et al., "Evaluation of sophorolipid biosurfactant production by Candida bombicola using animal fat," Bioresource Tech., 54(2): 143-150 (1995).

Gorin et al., "Hydroxy Fatty Acid Glycosides of Sophorose from Torulopsis Magnoliae," Can. J. Chem., 39(4): 846-855 (1961).

Gu et al., "A Study of the Scale-Up of Reversed-Phase Liquid Chromatography," Separation and Purification Technology, 15(1): 41-58 (1999).

Hirata et al., "Natural synergism of acid and lactone type mixed sophorolipids in interfacial activities and cytotoxicities," J. Oleo. Sci., 58(9): 565-572 (2009).

Hommel, "Formation and physiological role of biosurfactants produced by hydrocarbon-utilizing microorganisms. Biosurfactants in hydrocarbon utilization," Physiology of Biodegradative Microorganisms, 1(2-3): 107-119 (1990).

Liu et al., "Progress on biosynthesis and application of sophorolipids," Food Drug., 1(11):51-55 (2009).

Ma et al., "Effects of nitrogen sources on production and composition of sophorolipids by Wickerhamiella domercqiae var. sophorolipid CGMCC 1576," Appl. Microbiol. Biotechnol., 91(6): 1623-1632 (2011).

Nuñez et al., "LC/MS analysis and lipase modification of the sophorolipids produced by Rhodotorula bogoriensis," Biotechnol. Lett., 26(13): 1087-1093 (2004).

Okamoto, "Recent developments of Draize eye test alternative in Japan," Fragrance Journal, 2: 67-71 (2005).

Rau et al., "Sophorolipids: a source for novel compounds," Industrial Crops Products, 13(2): 85-92 (2001).

Saerens et al., "One-step production of unacetylated sophorolipids by an acetyltransferase negative Candida bombicola," Biotechnol. Bioeng., 108(12): 2923-2931 (2011).

Shah et al., "Sophorolipids, microbial glycolipids with anti-human immunodeficiency virus and sperm-immobilizing activities," Antimicrob. Agents Chemother., 49(10): 4093-4100 (2005).

Shah et al., "Utilization of Restaurant Waste Oil as a Precursor for Sophorolipid Production," Biotechnology Prog., 23(2): 512-515 (2007).

Song et al., "Structure characterization and physi-chemical properties of sophorolipid biosurfactants," Environmental Chemistry, 30(8): 1474-1479 (2011).

Tulloch et al., "A new hydroxy fatty acid sophoroside from Candida bogoriensis," Can. J. Chem., 46(3): 345-348 (1968).

Tulloch et al., "Structure and reactions of lactonic and acidic sophorosides of 17-hydroxyoctadecanoicacid," Can. J. Chem. 46: 3337-3351 (1968).

Van Bogaert et al., "Microbial production and application of sophorolipids," Appl. Microbiol. Biotechnol., 76(1): 23-34 (2007).

Zhou et al., "Production of sophorose lipids by Torulopsis bombicola from safflower oil and glucose," J. American Oil Chern Soc., 69(1): 89-91 (1992).

Zhou et al., "Supramolecular Assemblies of a Naturally Derived Sophorolipid," Langmuir, 20(19): 7926-7932 (2004).

Chinese Patent Office, Office Action in Chinese Patent Application No. 201480054091.5 (dated Oct. 29, 2018).

European Patent Office, Extended European Search Report in European Patent Application No. 14843085.3 (dated Feb. 23, 2017).

European Patent Office, Extended European Search Report in European Patent Application No. 14834955.8 (dated Nov. 16, 2016).

European Patent Office, Communication Purusant to Article 94(3) EPC in European Patent Application No. 14834955.8 (dated Jul. 21, 2017).

Japanese Patent Office, International Search Report in International Patent Application No. PCT/JP2014/070788 (dated Nov. 11, 2014).

Japanese Patent Office, Written Opinion of the International Searching Authority in International Patent Application No. PCT/JP2014/070788 (dated Nov. 11, 2014).

Japanese Patent Office, International Search Report in International Patent Application No. PCT/JP2014/073356 (dated Dec. 2, 2014).

Japanese Patent Office, Written Opinion of the International Searching Authority in International Patent Application No. PCT/JP2014/073356 (dated Dec. 2, 2014).

Japanese Patent Office, International Search Report in International Patent Application No. PCT/JP2018/008865 (dated Apr. 3, 2018).

Yatim, "Biotransformation of Palm Olein into Sophorolipid Biosurfactant," Doctor of Philosophy Thesis, University of New South Wales (2008).

European Patent Office, Communication Pursuant to Rule 114(2) EPC in European Patent Application No. 14834955.8 (dated Jun. 19, 2020).

U.S. Appl. No. 14/382,480, filed Sep. 2, 2014.
U.S. Appl. No. 14/911,174, filed May 23, 2016.
U.S. Appl. No. 15/061,330, filed Mar. 4, 2016.

European Patent Office, Third Party Observations for European Patent Application No. 14834955.8 (dated Jun. 19, 2020).

Japanese Patent Office, International Search Report in International Patent Application No. PCT/JP2020/001088 (dated Mar. 10, 2020).

(56) References Cited

OTHER PUBLICATIONS

Japanese Patent Office, Notice of Reasons for Refusal in Japanese Patent Application No. 2018-568976 (dated Jan. 22, 2019).

* cited by examiner

DETERGENT COMPOSITION COMPRISING AN ACIDIC SOPHOROSE LIPID AND FATTY ACID SALT MIXTURE

CROSS-REFERENCE TO RELATED APPLICATIONS

The present application is the U.S. national phase of International Patent Application No. PCT/JP2018/008865, filed Mar. 7, 2018, which claims priority to the specification of Japan Patent Application No. 2017-043340, filed on Mar. 7, 2017 and International Application No. PCT/JP2017/041133, filed on Nov. 15, 2017, the entire disclosures of which are incorporated in the present specification by reference.

TECHNICAL FIELD

The present application claims priority to the specification of Japan Patent Application No. 2017-043340, filed on Mar. 7, 2017 and International Application No. PCT/JP2017/041133, filed on Nov. 15, 2017, the entire disclosures of which are incorporated in the present specification by reference.

The present invention relates to a cleaning agent composition having good storage stability, especially storage stability at low temperature. The present invention also relates to a cleaning agent composition that can be favorably dispensed from a dispenser. The present invention further relates to a cleaning agent composition that exhibits good foamability and foam firmness. The present invention furthermore relates to a cleaning agent composition that not only exhibits good foamability and foam firmness, but also ensures good foam quality and is pleasant to the skin while imparting a comfortable feeling during washing.

BACKGROUND ART

Cleaning agents are used for washing the body (e.g., hair and body, including hands and face), dishes, houses, clothes, and anything in daily life. Cleaning agents have the effects of removing stains, removing bacteria to prevent infection, and removing and suppressing odor, as well as the effect of making the user feel refreshed by washing. In particular, hand soaps, body soaps, shampoos, kitchen detergents, etc. are used routinely almost every day. Such cleaning agents are thus desired not only to have fundamental functions, such as detergency, but also to be able to be used comfortably without stress. Specifically, it is desired that cleaning agents have excellent storage stability, do not cause precipitation or separation even when used under conditions at low temperature, can be repeatedly dispensed from a container such as a manual or automatic dispenser stably without excessive burden, exhibit good foamability and foam firmness, ensure good foam quality that is pleasant to the skin (sensation during contact) while imparting a comfortable feeling during washing, and do not cause an unpleasant slippery feel during rinsing, skin tightening sensation, or a squeaky feel.

In particular, a slippery feel during rinsing and skin tightening sensation and a squeaky feel after washing are known to be caused by a synthetic surfactant or soap (fatty acid salt), which is contained as a cleaning and foaming component in a cleaning agent, remaining on the skin. Several methods have been reported to solve these problems. For example, it has been reported that the problems (a slippery feel, skin tightening sensation, and a squeaky feel) during rinsing or after washing can be solved by using a surfactant in combination with a sophorose lipid to inhibit the surfactant from sticking to and accumulating on the body (see, for example, Patent Literature 1).

Sophorose lipids, which are a type of glycolipid biosurfactant produced by microorganisms (natural surfactant) (Non-patent Literature 1), cause less skin irritation and are good for the natural environment. In this sense, sophorose lipids have properties in common with soap, which is a natural cleaning agent with high safety and biodegradability. Thus, the present applicant previously found that using soap (fatty acid salt) in combination with a sophorose lipid improves weaknesses of soap, such as low solubility and poor foaming under hard water conditions, while taking advantage of soap (safety and biodegradability), and further improves moisture-retaining properties, and the present applicant proposed a cleaning agent composition containing soap and a sophorose lipid (see, for example, Patent Literature 2).

CITATION LIST

Patent Literature

PTL 1: JP2009-275145A
PTL 2: JP2006-083238A

Non-Patent Literature

NPL 1: Canadian Journal of Chemistry, 39, 846 (1961)

SUMMARY OF INVENTION

Technical Problem

As described above, use of soap in combination with a sophorose lipid improves low solubility of soap and poor foaming of soap under hard water conditions while taking advantage of soap (safety and biodegradability) and suppresses skin tightening sensation and a squeaky feel after washing. However, use of soap in combination with a sophorose lipid is problematic in that it loses the inherent creaminess of soap and decreases washing comfort. Further, use of soap in combination with a sophorose lipid has the risk that the storage stability, especially storage stability at low temperature ("stability at low temperature") may decrease, causing precipitation during distribution and storage or during use. This drawback can be improved to some degree by increasing the proportion of soap; however, it was found that increasing the proportion of soap causes the problem that when such a cleaning agent is stored in a dispenser and used, the dispensing outlet becomes clogged.

An object of the present invention is to provide a cleaning agent composition that enables solving the above problems caused by using soap in combination with a sophorose lipid ("SL"), and not only has detergency, which is a fundamental function, but also can be used comfortably in daily life without stress.

Specifically, an object of the present invention is to provide a cleaning agent composition comprising a fatty acid salt, which is soap, and an SL in which the storage stability, especially stability at low temperature, is improved, and occurrence of precipitation is significantly suppressed during use.

Another object of the present invention is to provide a cleaning agent composition comprising a fatty acid salt and an SL in which the composition exhibits improved dispensing ability and can be dispensed without clogging even when stored in a dispenser and used.

A further object of the present invention is to provide a cleaning agent composition comprising a fatty acid salt and an SL in which the composition exhibits improved foamability and foam firmness and lathers well, and the foam lasts for a moderate period.

A still further object of the present invention is to provide a cleaning agent composition comprising a fatty acid salt and an SL in which the composition ensures improved foam quality and is pleasant to the skin (sensation during contact) while imparting a comfortable feeling during washing.

Solution to Problem

The present inventors conducted extensive research to solve the above problems of the prior art and found that a cleaning agent composition that enables the above problems to be solved can be prepared by using a fatty acid salt and an SL in specific proportions in combination. The present invention has been accomplished based on this finding and includes the following embodiments.

(I) Cleaning Agent Composition (I-1) A cleaning agent composition comprising (a) at least one fatty acid salt (excluding triethanolamine salts of fatty acids) and (b) an SL,
wherein
A) the proportion of the total amount of the component (a) is 4 to 18 mass % based on the cleaning agent composition taken as 100 mass %;
B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
C) the proportion of an acidic SL is 80 mass % or more based on the total amount of the component (b) taken as 100 mass %; and
D) the proportion of the total amount of the component (b) is 5 to 80 parts by mass per 100 parts by mass of the total amount of the component (a).

(I-2) The cleaning agent composition according to (I-1), wherein (a) the at least one fatty acid salt comprises salts of two or more fatty acids selected from the group consisting of $C_{8-22}$ saturated fatty acids and unsaturated fatty acids.

(I-3) The cleaning agent composition according to (I-1) or (I-2), wherein (a) the at least one fatty acid salt is a salt of at least one fatty acid selected from the group consisting of capric acid, lauric acid, myristic acid, palmitic acid, oleic acid, coconut oil fatty acid, and palm kernel fatty acid.

(I-4) The cleaning agent composition according to any one of (I-1) to (I-3), wherein the proportion of an acidic SL is 100 mass % based on the total amount of the component (b) taken as 100 mass %.

(I-5) The cleaning agent composition according to any one of (I-1) to (I-4), wherein
E-1) the proportion of the total amount of the component (b) is 50 parts by mass or less per 100 parts by mass of the total amount of the component (a).

(I-6) The cleaning agent composition according to (I-5), wherein
E-2) the proportion of the total amount of the component (b) is 10 parts by mass or more per 100 parts by mass of the total amount of the component (a); and
F) based on 100 parts by mass of the total amount of the component (a), F-1) the proportion of a lauric acid salt is 15 to 80 parts by mass,
F-2) the proportion of a myristic acid salt is 10 to 50 parts by mass,
F-3) the proportion of the total amount of a palmitic acid salt and an oleic acid salt is 5 to 60 parts by mass, and
F-4) the proportion of the total amount of fatty acid salts other than lauric acid salts, myristic acid salts, palmitic acid salts, and oleic acid salts is less than 10 parts by mass.

(I-7) A cleaning agent composition for dispensers in which the cleaning agent composition according to any one of (I-1) to (I-6) is placed in the storage portion of a container comprising a storage portion and a dispensing portion that comprises a dispensing mechanism.

(I-8) The cleaning agent composition for dispensers according to (I-7), wherein the container comprising a storage portion and a dispensing portion that comprises a dispensing mechanism is a dispenser comprising a dispensing portion that comprises a liquid-dispensing mechanism or a dispenser comprising a dispensing portion that comprises a foam-forming mechanism and a foam-dispensing mechanism.

(I-9) The cleaning agent composition for dispensers according to (I-8), wherein the dispenser is a pump dispenser or an auto-dispenser comprising a mechanism for automatically dispensing contents to the outside with a sensor (also referred to as a "sensor dispenser").

(II) Method for Improving Storage Stability and/or Dispensing Ability from Dispenser (II-1) A method for improving storage stability and/or dispensing ability from a dispenser of a cleaning agent composition comprising (a) at least one fatty acid salt (excluding triethanolamine salts of fatty acids) and (b) an SL, the method comprising preparing the composition such that
A) the proportion of the total amount of the component (a) is 4 to 18 mass % based on the cleaning agent composition taken as 100 mass %;
B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
C) the proportion of an acidic SL is 80 mass % or more based on the total amount of the component (b) taken as 100 mass %; and
D) the proportion of the total amount of the component (b) is 5 to 80 parts by mass per 100 parts by mass of the total amount of the component (a).

(II-2) The method according to (II-1), wherein (a) the at least one fatty acid salt comprises salts of two or more fatty acids selected from the group consisting of $C_{8-22}$ saturated fatty acids and unsaturated fatty acids.

(II-3) The method according to (II-1) or (II-2), wherein the proportion of an acidic SL is 100 mass % based on the total amount of the component (b) taken as 100 mass %.

(II-4) The method according to any one of (II-1) to (II-3), wherein the dispenser is a pump dispenser or a sensor dispenser.

(III) Method for Improving Storage Stability, Dispensing Ability from Dispenser, Foamability, and/or Foam Firmness (III-1) A method for improving storage stability, dispensing ability from a dispenser, foamability, and/or foam firmness of a cleaning agent composition comprising (a) at least one fatty acid salt (excluding triethanolamine salts of fatty acids) and (b) an SL, the method comprising preparing the composition such that A) the proportion of the total amount of the component (a) is 4 to 18 mass % based on the cleaning agent composition taken as 100 mass %;
B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
C) the proportion of an acidic SL is 80 mass % or more based on the total amount of the component (b) taken as 100 mass %;
D) the proportion of the total amount of the component (b) is 5 to 80 parts by mass per 100 parts by mass of the total amount of the component (a); and
E-1) the proportion of the total amount of the component (b) is 50 parts by mass or less per 100 parts by mass of the total amount of the component (a).
(III-2) The method according to (III-1), wherein (a) the at least one fatty acid salt comprises salts of two or more fatty acids selected from the group consisting of $C_{8}2$2 saturated fatty acids and unsaturated fatty acids.
(III-3) The method according to (III-1) or (III-2), wherein the proportion of an acidic SL is 100 mass % based on the total amount of the component (b) taken as 100 mass %.
(III-4) The method according to any one of (III-1) to (III-3), wherein the dispenser is a pump dispenser or a sensor dispenser.
(IV) Method for Improving Storage Stability, Dispensing Ability from Dispenser, Foamability, Foam Firmness, and/or Foam Texture
(IV-1) A method for improving stability at low temperature, dispensing ability from a dispenser, foamability, foam firmness, and/or foam texture of a cleaning agent composition comprising
(a) at least one fatty acid salt (excluding triethanolamine salts of fatty acids) and (b) an SL, the method comprising preparing the composition such that
A) the proportion of the total amount of the component (a) is 4 to 18 mass % based on the cleaning agent composition taken as 100 mass %;
B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
C) the proportion of an acidic SL is 80 mass % or more based on the total amount of the component (b) taken as 100 mass %;
D) the proportion of the total amount of the component (b) is 5 to 80 parts by mass per 100 parts by mass of the total amount of the component (a);
E) the proportion of the total amount of the component (b) is 10 to 50 parts by mass per 100 parts by mass of the total amount of the component (a); and
F) based on 100 parts by mass of the total amount of the component (a),
    F-1) the proportion of a lauric acid salt is 15 to 80 parts by mass,
    F-2) the proportion of a myristic acid salt is 10 to 50 parts by mass,
    F-3) the proportion of the total amount of a palmitic acid salt and an oleic acid salt is 5 to 60 parts by mass, and
    F-4) the proportion of the total amount of fatty acid salts other than lauric acid salts, myristic acid salts, palmitic acid salts, and oleic acid salts is less than 10 parts by mass.

(IV-2) The method according to (IV-1), wherein (a) the at least one fatty acid salt comprises salts of two or more fatty acids selected from the group consisting of $C_{8-22}$ saturated fatty acids and unsaturated fatty acids.
(IV-3) The method according to (IV-1) or (IV-2), wherein the proportion of an acidic SL is 100 mass % based on the total amount of the component (b) taken as 100 mass %.
(IV-4) The method according to any one of (IV-1) to (IV-3), wherein the dispenser is a pump dispenser or a sensor dispenser.

Advantageous Effects of Invention

The cleaning agent composition of the present invention, which comprises (a) a fatty acid salt and (b) an SL in proportions that satisfy features A, B, C, and D above, has excellent storage stability, especially stability at low temperature, and exhibits good dispensing ability from a dispenser. The cleaning agent composition of the present invention can be thus stored in, for example, a sensor dispenser, trigger dispenser, or pump dispenser and used daily for washing the body (e.g., hands, face, body, and hair), dishes, etc.

The cleaning agent composition of the present invention that satisfies feature E-1 in addition to the above features exhibits good foamability and/or foam firmness in addition to the properties described above. Thus, when the composition is placed in a foam dispensing-type container having a foam-forming mechanism and a foam-dispensing mechanism (preferably a dispenser) and used, it can be conveniently used in the form of foam. Even when the composition is placed in a liquid dispensing-type container and dispensed from the container, it can easily lather, for example, with hands or a net. Moreover, the cleaning agent composition of the present invention that further satisfies features E-2 and F (F-1 to F-4) in addition to the above features enables formation of foam that is pleasant to the skin while imparting a comfortable feeling during washing in addition to the properties described above. Thus, the composition gives the impression that it is gentle to the skin and can be used comfortably every day.

DESCRIPTION OF EMBODIMENTS (I) Cleaning Agent Composition
The cleaning agent composition of the present invention comprises (a) a fatty acid salt and (b) an SL as active ingredients. These components are described below.
(a) Fatty Acid Salt
The component (a) used in the present invention is composed of a fatty acid and a base, and any fatty acid salt usable as a component of soap can be used.
Examples of fatty acids include fatty acids selected from $C_{8-22}$ saturated fatty acids and unsaturated fatty acids. Examples of $C_{8-22}$ fatty acids include saturated fatty acids, such as caprylic acid, capric acid, lauric acid, myristic acid, palmitic acid, isopalmitic acid, stearic acid, isostearic acid, arachidic acid, and behenic acid; and unsaturated fatty acids, such as oleic acid, linoleic acid, linolenic acid, and arachidonic acid. These fatty acids may be used singly or in a combination of two or more.
Fatty acids selected from among $C_{10-20}$ saturated fatty acids and unsaturated fatty acids are preferable, and fatty acids selected from among $C_{10-18}$ saturated fatty acids and unsaturated fatty acids are more preferable. The component (a) of the present invention comprises at least one fatty acid salt having 12 or fewer carbon atoms among fatty acid salts formed from the fatty acids described above. Two or more of fatty acid salts having 12 or fewer carbon atoms may be used in any combination as long as the effects of the present invention are not impaired. Moreover, one or more of fatty acid salts having 14 or more carbon atoms may be used in any combination with one or two or more of fatty acid salts having 12 or fewer carbon atoms. Preferred examples of fatty acid salts having 12 or fewer carbon atoms include capric acid and lauric acid. Lauric acid is preferable. Preferred examples of fatty acids having 14 or more carbon atoms include myristic acid, palmitic acid, and oleic acid. Myristic acid is particularly preferable. Either palmitic acid or oleic acid may be used with or without myristic acid, or both palmitic acid and oleic acid may be used in combination. Preferably, palmitic acid and/or oleic acid is used in combination with myristic acid.

As fatty acids, mixed fatty acids that are derived from natural oils and fats and contain fatty acids described above may be used as long as they meet the requirements of the present invention in the form of salt and the effects of the present invention are attained. Examples of natural oils and fats include vegetable oils and fats, such as linseed oil, perilla oil, oiticica oil, olive oil, cacao oil, kapok oil, white mustard oil, sesame oil, rice bran oil, safflower oil, shea nut oil, China wood oil, soybean oil, tea seed oil, camellia oil, corn oil, rapeseed oil, palm oil, palm kernel oil, castor oil, sunflower oil, cottonseed oil, coconut oil, Japan wax, and peanut oil; and animal oils and fats, such as horse fat, beef tallow, lard, goat fat, milk fat, fish fat, and whale oil. The mixed fatty acids are those that are derived from natural oils and fats and contain fatty acids having 8 to 22 carbon atoms, preferably 10 to 20 carbon atoms, and more preferably 10 to 18 carbon atoms, as described above. Specific examples include coconut oil fatty acid, palm kernel oil fatty acid, beef tallow fatty acid, and the like that contain at least one fatty acid having 12 or fewer carbon atoms. Fatty acids derived from vegetable oils and fats, such as coconut oil fatty acid and palm kernel oil fatty acid, are preferable. Salts of mixed fatty acids derived from natural oils and fats may be used in any combination with one or more of salts of the individual fatty acids described above. For reference, Table 1 shows an example of the proportions of fatty acids contained in coconut oil fatty acid and palm kernel oil fatty acid (Keiichi Inaba. *Shibosan Kagaku* [Fatty Acid Chemistry]. New ed. Saiwai Shobo). In Table 1, each constituent fatty acid is indicated by the number of carbon atoms of the fatty acid, and the number after the hyphen indicates the number of double bonds. However, the proportion of each fatty acid below is an example, and the present invention is not limited to these.

Examples of counterions (bases) that react a fatty acid described above to form a fatty acid salt include ions of alkali metals, such as lithium, sodium, and potassium; alkanolamines other than triethanolamine, such as diethanolamine, aminomethyl propanol, and tromethamine; basic amino acids, such as arginine and lysine; ammonium; and the like. Ions of alkali metals such as sodium and potassium, and diethanolamine are preferable. Ions of alkali metals such as sodium and potassium are more preferable, and potassium ions are particularly preferable.

As described above, preferable examples of the component (a) include alkali metal salts of fatty acids, in particular, potassium salts of fatty acids. Thus, preferred examples of fatty acid salts having 12 or fewer carbon atoms usable as the component (a) include alkali metal salts, in particular a potassium salt, of at least one fatty acid selected from the group consisting of capric acid and lauric acid. Preferred examples of fatty acid salts having 14 carbon atoms usable as the component (a) include alkali metal salts of myristic acid, in particular potassium myristate. Further, preferred examples of fatty acid salts having 16 or more carbon atoms usable as the component (a) include alkali metal salts, in particular a potassium salt, of at least one fatty acid selected from the group consisting of palmitic acid and oleic acid.

The amount of the component (a) in the cleaning agent composition of the present invention is generally 4 to 18 mass % (feature A). When the amount of the component (a) is significantly less than 4 mass %, the storage stability, especially storage stability under low-temperature conditions at a temperature of 5° C. or less (stability at low temperature), decreases, and precipitation tends to occur due to storage under such conditions (see Comparative Examples 1 and 3). When the amount of the component (a) is significantly greater than 18 mass %, the dispensing ability from a pump dispenser tends to decrease (see Comparative Example 4). Accordingly, the lower limit of the component (a) may be 4 mass % or more, and may be 5 mass % or more, or 6 mass % or more. The upper limit of the component (a) may be 18 mass % or less, and may be 15 mass % or less, or 13 mass % or less. Any combination of these lower limit values and upper limit values may be selected. The amount of the component (a) in the range of, for example, 5 to 15 mass % or 6 to 13 mass %, may be selected.

Based on 100 parts by mass of the total amount of the component (a) contained in the cleaning agent composition of the present invention, the proportion of the total amount of one or more fatty acid salts having 12 or fewer carbon atoms contained in the component (a) is 15 parts by mass or more, and the proportion of the total amount of one or more

TABLE 1

| Fatty acid proportion (mass proportion) in coconut oil fatty acid (based on the whole taken as 100 mass %) | | | | | | | | | |
|---|---|---|---|---|---|---|---|---|---|
| | Constituent fatty acid | | | | | | | | |
| | C8 | C10 | C12 | C14 | C16 | C18 | C18-1 | C18-2 | Others |
| Constituent proportion | 8 | 6 | 44 | 16 | 8 | 3 | 5 | 2 | 8 |

| Fatty acid proportion (mass proportion) in palm kernel oil fatty acid (based on the whole taken as 100 mass %) | | | | | | | | | |
|---|---|---|---|---|---|---|---|---|---|
| | Constituent fatty acid | | | | | | | | |
| | C8 | C10 | C12 | C14 | C16 | C18 | C18-1 | C18-2 | Others |
| Constituent proportion | 3 | 3 | 46 | 16 | 8 | 2 | 11 | — | 11 | fatty acid salts having 16 or more carbon atoms contained in the component (a) is 60 parts by mass or less (feature B). The proportion of the total amount of one or more fatty acid salts having 12 or fewer carbon atoms is preferably 30 parts by mass or more, and more preferably 45 parts by mass or more, and the upper limit is 90 parts by mass. The proportion of the total amount of one or more fatty acid salts having 16 or more carbon atoms is preferably 50 parts by mass or less, and more preferably 40 parts by mass or less, and the lower limit is 0 parts by mass. Any combination of the above values of the proportion of the total amount of one or more fatty acid salts having 12 or fewer carbon atoms and the above values of the proportion of the total amount of one or more fatty acid salts having 16 or more carbon atoms may be selected. When the proportion of the total amount of one or more fatty acid salts having 12 or fewer carbon atoms is significantly less than 15 parts by mass and/or when the proportion of the total amount of one or more fatty acid salts having 16 or more carbon atoms is significantly greater than 60 parts by mass, the storage stability, especially storage stability under low-temperature conditions at a temperature of 5° C. or less (stability at low temperature), decreases, and the dispensing ability from a pump dispenser tends to decrease (see Comparative Examples 1 and 2).

As shown in Examples 1 to 11, a cleaning agent composition comprising the components (a) and (b), wherein the proportion of the component (a) is 4 to 18 mass %; based on 100 parts by mass of the total amount of the component (a), the total amount of one or more fatty acid salts having 12 or fewer carbon atoms is 15 parts by mass or more, and the total amount of one or more fatty acid salts having 16 or more carbon atoms is 60 parts by mass or less, as described above, has good storage stability, especially storage stability under low-temperature conditions at a temperature of 5° C. or less (stability at low temperature), and good dispensing ability (liquid dispensing ability, foam dispensing ability) from a pump dispenser (see Examples 1 to 11).

As described above, the cleaning agent composition of the present invention, which satisfies features A and B, has good storage stability and dispensing ability (liquid dispensing ability, foam dispensing ability) from a pump dispenser. Further, setting the proportion of an acidic SL in the total amount of the component (b) (100 mass %) to 80 mass % or more (feature C) and setting the proportion of the component (b) to 5 to 80 parts by mass per 100 parts by mass of the total amount of the component (a) (feature D) improve dispensing ability from an auto-dispenser (sensor dispenser) having a mechanism for automatically dispensing contents to the outside with a sensor (Examples 12 to 14). A cleaning agent composition placed in a pump or trigger dispenser, both of which are pushed by hand, can be dispensed to the outside by applying any force as necessary. On the other hand, sensor dispensers have a mechanism in which a cleaning agent composition in such a dispenser is dispensed by an almost constant force; thus, in sensor dispensers, slight clogging causes significant abnormality in the dispensing direction and difficulty in dispensing. Accordingly, cleaning agent compositions are required to have even better dispensing ability and storage stability. Examples of causes of abnormality in the dispensing direction due to clogging include formation of a fine precipitate in a cleaning agent composition, evaporation and solidification of liquid remaining inside the pump or at the dispensing outlet, and the like. The cleaning agent composition of the present invention, which satisfies features A, B, C, and D, has the effect of minimizing and improving these causes. The cleaning agent composition of the present invention can be thus suitably placed in a sensor dispenser and used.

As feature C, the proportion of an acidic SL in the total amount of the component (b) (100 mass %) may be 80 mass % or more, preferably 85 mass % or more, more preferably 90 mass % or more, and even more preferably 95 mass % or more. The acidic SL may account for 100 mass % of the component (b).

As feature D, the proportion of the component (b) may be 5 to 80 parts by mass, preferably 5 to 70 parts by mass, and more preferably 8 to 60 parts by mass, per 100 parts by mass of the total amount of the component (a).

Moreover, the proportion of each fatty acid salt contained in the component (a) is not limited and may be, for example, as follows, based on 100 parts by mass of the total amount of the component (a) contained in the cleaning agent composition of the present invention (feature F):

(F-1) the proportion of a lauric acid salt: 15 to 80 parts by mass;
(F-2) the proportion of a myristic acid salt: 10 to 50 parts by mass;
(F-3) the proportion of the total amount of a palmitic acid salt and an oleic acid salt: 5 to 60 parts by mass; and
(F-4) the proportion of the total amount of fatty acid salts other than the above: less than 10 parts by mass.

Feature F affects the foam quality of the cleaning agent composition. In particular, when the proportion of a lauric acid salt is significantly greater than 80 parts by mass based on the whole component (a) and/or when the proportion of the total amount of a palmitic acid salt and an oleic acid salt is significantly less than 5 parts by mass, the foam quality of the cleaning agent composition tends to be unsatisfactory. More specifically, the cleaning agent composition of the present invention that satisfies features A, B, C, and D has good storage stability and dispensing ability, and the cleaning agent composition of the present invention that further satisfies features A, B, C, and D, as well as feature E-1 described later, exhibits good foamability and foam firmness in addition to the above properties; however, in this case, the foam quality tends to be unsatisfactory. On the other hand, as shown in Examples 5 to 14, the cleaning agent composition of the present invention that satisfies feature F in addition to features A, B, C, and D, as well as feature E, exhibits good foam quality in addition to storage stability, especially storage stability under low-temperature conditions at a temperature of 5° C. or less (stability at low temperature) and dispensing ability (liquid dispensing ability, foam dispensing ability) from a dispenser, as well as foamability and foam firmness. Here, the phrase "cleaning agent composition that exhibits good foam quality" specifically means that foam that is pleasant to the skin (sensation during contact) while imparting a comfortable feeling during washing can be formed.

A preferred embodiment of feature F is as follows: based on 100 parts by mass of the total amount of the component (a) contained in the cleaning agent composition of the present invention, (F-1) the proportion of a lauric acid salt: preferably 20 to 75 parts by mass, and more preferably 30 to 75 parts by mass;
(F-2) the proportion of a myristic acid salt: preferably 10 to 45 parts by mass, and more preferably 10 to 35 parts by mass;
(F-3) the proportion of the total amount of a palmitic acid salt and an oleic acid salt: preferably 5 to 50 parts by mass, and more preferably 5 to 40 parts by mass; and (F-4) the proportion of the total amount of fatty acid salts other than the above: preferably 0 to 8 parts by mass, and more preferably 0 to 5 parts by mass.

(b) Sophorose Lipid (SL)

The SL of the component (b) used in the cleaning agent composition of the present invention is a glycolipid consisting of a hydroxyl fatty acid, and sophorose or a sophorose whose one or more hydroxyl groups are acetylated. Sophorose is a sugar consisting of two glucose molecules bound through a β1→2 bond. A hydroxyl fatty acid is a fatty acid having a hydroxyl group.

SL is roughly classified into acidic SL represented by Formula 1 below and lactonic SL represented by Formula 2 below. Acidic SL is a sophorose lipid in which the carboxyl group of the hydroxyl fatty acid is free. Lactonic SL is a sophorose lipid in which the carboxyl group of the hydroxyl fatty acid is bound to the sophorose in the molecule.

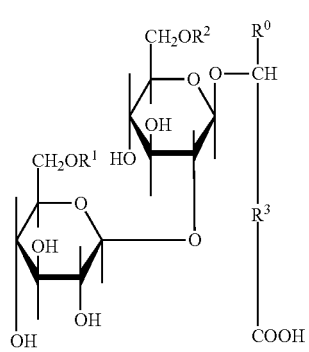

Formula 1

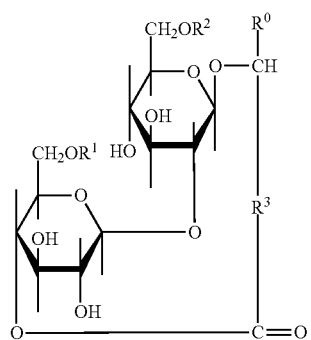

Formula 2

In Formulas 1 and 2, $R^0$ is either a hydrogen atom or a methyl group. $R^1$ and $R^2$ are each independently a hydrogen atom or an acetyl group. $R^3$ is composed of a saturated aliphatic hydrocarbon chain, or an unsaturated aliphatic hydrocarbon chain having at least one double bond. The aliphatic hydrocarbon chain generally has 11 to 20 carbon atoms, preferably 13 to 17 carbon atoms, and more preferably 14 to 16 carbon atoms. The SL referred to herein includes a salt of an acidic sophorose lipid represented by Formula 1 above. Examples of the salt include salts of alkali metals, such as potassium and sodium, salts of alkaline earth metals, such as magnesium and calcium, and ammonium salts. Salts of alkali metals are preferable, and potassium salts and sodium salts are more preferable.

The term "sophorose lipid (SL)" as used herein does not distinguish between lactonic SL, acidic SL, and a salt thereof. In this case, the sophorose lipid (SL) may be lactonic SL, acidic SL, or a salt thereof, or may comprise a mixture of two or more of these. When the term "sophorose lipid (SL)" refers to either of them, it is referred to as "acidic SL" or "lactonic SL." Unless otherwise stated, the meaning of the term "acidic SL" include both acidic SL in free form and acidic SL in salt form. Acidic SL and lactonic SL each may be a single compound in which each of $R^0$ to $R^3$ is a specific atom or substituent in the above formulas, or may be a mixture (composition) of multiple compounds having various $R^0$ to $R^3$.

Specifically, SL is obtained by culturing a microorganism, especially a yeast. SL obtained by yeast fermentation includes both the acidic SL and lactonic SL described above. Examples of SL-producing yeasts include *Starmerella (Candida) bombicola, C. apicola, C. petrophilum, Rhodotorula (Candida) bogoriensis*, and the like. By culturing such a yeast using a medium containing a high concentration of a sugar and an oily substrate, a large amount (100 to 150 g/L) of SLs can be produced and accumulated in the medium. The SLs can be separated by subjecting the culture to purification treatment, such as centrifugation, decantation, or ethyl acetate extraction, and can be obtained as a dark-brown candy-like substance by further washing the SLs with hexane. Since SLs has a greater specific gravity than water, it can be easily removed in such a manner that the culture is allowed to stand after completion of culturing to thereby separate the SLs by settling into the lower layer. The SLs thus obtained are SLs with a water content of about 50 mass %. The obtained SLs are a mixture of multiple compounds represented by Formulas 1 and 2, as described above. These SLs are roughly classified into acidic SL and lactonic SL.

In the present invention, the component (b) may be acidic SL, lactonic SL, or a mixture of both. From the viewpoint of product stability (e.g., pH stability, and suppression of a change in appearance (such as precipitation) associated with a pH change), the component (b) is preferably acidic SL.

Acidic SL can be prepared by subjecting a mixture of acidic SL and lactonic SL obtained by the method described above to alkaline treatment and hydrolyzing ester linkages in lactonic SL. Examples of alkaline treatment include an alkaline reflux method (e.g., JP2006-070231A); however, the alkaline treatment is not limited to this method, and known alkaline treatment methods can be used. For the sake of convenience, commercially available acidic SL can be used. For example, acidic SL is sold, for example, from Saraya Co., Ltd., under the trade name SOFORO (registered trademark) AC-30. This product is an acidic SL with a water content of 70 mass %.

The proportion of the component (b) in the cleaning agent composition of the present invention is preferably adjusted to 50 parts by mass or less per 100 parts by mass of the total amount of the component (a) in the cleaning agent composition (feature E-1). The proportion of the component (b) in the cleaning agent composition of the present invention is preferably 40 parts by mass or less, and more preferably 30 parts by mass or less, per 100 parts by mass of the total amount of the component (a) in the cleaning agent composition. When the proportion of the component (b) is significantly greater than 50 parts by mass per 100 parts by mass of the total amount of the component (a), the foamability and foam firmness of the cleaning agent composition tend to decrease. That is, the cleaning agent composition of the present invention that has features A, B, C, and D, as well as feature E-1, is excellent in foamability in addition to storage stability and dispensing ability, and the firmness of formed foam is also excellent.

The proportion of the component (b) in the cleaning agent composition of the present invention is preferably adjusted to 10 parts by mass or more per 100 parts by mass of the total amount of the component (a) in the cleaning agent composition (feature E-2). The proportion of the component (b) in the cleaning agent composition of the present invention is preferably 13 parts by mass or more, and more preferably 15 parts by mass or more, per 100 parts by mass of the total amount of the component (a) in the cleaning agent composition. When the proportion of the component (b) is significantly less than 10 parts by mass per 100 parts by mass of the total amount of the component (a), the quality of formed foam tends to decrease, and the foam tends not to be pleasant to the skin and tends not to impart a comfortable feeling during washing. That is, the cleaning agent composition of the present invention that has features A, B, C, D, and E-1, as well as features E-2 and F, is excellent in foamability and foam firmness in addition to storage stability and dispensing ability, and the foam quality is also excellent. Any combination of the upper limit values (feature E-1) and lower limit values (feature E-2) of the proportion of the component (b) per 100 parts by mass of the total amount of the component (a) may be selected. The proportion of the component (b) per 100 parts by mass of the total amount of the component (a) is, for example, 10 to 50 parts by mass or 13 to 40 parts by mass.

The amount (on a solids basis (%)) of the component (b) in the cleaning agent composition of the present invention (100 mass %) is, for example, generally 0.01 to 10 mass % and can be set in this range so that feature E described above (E-1, E-2) is not hindered. The amount of the component (b) is preferably 0.4 to 9 mass %.

From the viewpoint of foamability, foam firmness, and skin irritation, it is desirable that the cleaning agent composition of the present invention is adjusted to have a pH in the range of 9 to 11, and preferably 9.5 to 10.5, using a pH adjuster. Examples of pH adjusters include acids, alkali metal salts, and the like. Examples of acids include organic acids selected from citric acid, malic acid, succinic acid, and the like; and inorganic acids, such as sulfuric acid and hydrochloric acid. Examples of alkali metal salts include potassium hydroxide, sodium hydroxide, potassium carbonate, and the like.

The remainder of the cleaning agent composition of the present invention is adjusted using water. The cleaning agent composition of the present invention may contain as an optional component one or more other components, such as a thickener (viscous agent), a humectant (moisturizing agent), an antiphlogistic agent, a chelating agent, a pigment, a perfume, an antioxidant, a preservative, and a disinfectant, according to the purpose or use as long as the effects of the present invention are not impaired. The water used in the present invention may be any water as long as the effects of the present invention are not impaired. Preferred examples of the water include purified water, distilled water, ion-exchanged water, and RO water. When tap water, which is considered to have a hardness commonly of 300 mg/l or less (according to the ministerial ordinance relating to the water quality standard of the Japanese Water Supply Act), typically about 10 to 100 mg/l, is used, it is preferable that tap water is used in combination with a chelating agent to sequester minerals contained in the tap water. The amount of the chelating agent used is not limited as long as minerals can be sequestered. The amount of the chelating agent may be, for example, about 0.1 mass %. The water hardness can be determined using the following formula.

$$\text{Hardness} = (\text{calcium amount (mg/l)} \times 2.5) + (\text{magnesium amount (mg/l)} \times 4)$$

The thickener can be used to increase the viscosity of the cleaning agent composition. A wide variety of thickeners that can be generally added to cleaning agents can be used as long as the effects of the present invention are not impaired. Examples include carboxy vinyl polymers (carbomer), xanthan gum, guar gum, gelatin, hydroxypropyl cellulose, ethyl hydroxyethyl cellulose, and like modified celluloses, bentonite, and sodium polyacrylate.

The humectant (moisturizing agent) acts to retain water. The humectant can also be used to make the components of the cleaning agent composition readily compatible with each other, prevent drying, and hydrate and soften the skin when used. Any humectant can be used as long as the effects of the present invention are not impaired. Specific examples include polyhydric alcohols, such as glycerin, butylene glycol, propanediol, hexylene glycol, dipropylene glycol, propylene glycol, hexanediol, pentanediol, octanediol, decanediol, diglycerin, and ethylhexylglycerin; amino acids, such as taurine, glutamic acid, glycine, leucine, serine, valine, threonine, alanine, isoleucine, allantoin, phenylalanine, arginine, proline, and tyrosine; and extracts of natural origin, such as perilla extract, rosemary extract, royal jelly extract, and placenta extract. Natural moisturizing factors (NMFs) are also usable. Polyhydric alcohols are preferable.

The chelating agent can be added to sequester metal ions contained in the cleaning agent composition to prevent obstructions due to metal ions (e.g., decreased foaming). Any chelating agent can be used as long as the effects of the present invention are not impaired. Specific examples include salts of organic aminocarboxylic acids, such as EDTA, NTA, DTPA, GLDA, HEDTA, GEDTA, TTHA, HIDA, and DHEG.

Examples of antiphlogistic agents include, but are not limited to, allantoin, dipotassium glycyrrhizate, and the like.

The perfume can be used as a single perfume component or a composition containing multipole perfume components to mask the raw material odor or improve preference. Any perfume can be used as long as the effects of the present invention are not impaired. Specific examples include synthetic perfumes, such as alcohol-based perfumes, aldehyde-based perfumes, ether-based perfumes, ester-based perfumes, ketone-based perfumes, and lactone-based perfumes; and natural perfumes from plants. The natural perfumes include, but are not limited to, perfumes prepared from essential oils, or distillates or fractions thereof. Such essential oils are obtained using a plant (e.g., a flower, leaf, fruit, pericarp, bark, root, seed) as a raw material.

The cleaning agent composition of the present invention can be prepared by mixing the component (a), the component (b), and, if necessary, one or more optional components described above, together with water. In the process of preparing the cleaning agent composition, instead of using (adding and blending) the component (a) itself, the component (a), which comprises a fatty acid salt, may be produced by stirring a fatty acid constituting the component (a) and a hydroxide of a salt constituting the component (a) while heating to carry out a neutralization reaction. The cleaning agent composition prepared in such a manner can be adjusted to have a pH of 9 to 11 using a pH adjuster, as described above, and provided as the cleaning agent composition of the present invention.

The cleaning agent composition of the present invention prepared by the method described above can be placed in a container and provided to the market. The container may be any container (including a pouch pack container such as a refill container) that has a mouth portion (outlet) and a storage portion. The container is preferably a container having a dispensing portion comprising a dispensing mechanism. The container may have as the dispensing mechanism a mechanism for dispensing the cleaning agent composition of the present invention, which is an aqueous liquid composition, as is to the outside in the form of liquid from the container (liquid-dispensing mechanism) or may have a mechanism for forming foam by introducing air when the cleaning agent composition of the present invention is dispensed from the container (foam-forming mechanism) and a mechanism for dispensing formed foam to the outside in the form of foam (foam-dispensing mechanism).

The container is preferably a container having a mechanism for dispensing a predetermined amount of the cleaning agent composition to the outside from the container in one action of dispensing (e.g., pushing a pump, pulling a trigger, or putting a hand above a sensor) (which may be referred to as a "dispenser" in the present invention). The dispensing mechanism of the dispenser is not limited and includes a sensor mechanism, spray mechanism, trigger mechanism, aerosol mechanism, and pump mechanism. The trigger dispenser is a container in which a trigger sprayer for dispensing the cleaning agent composition is attached to the mouth portion of the container body (trigger spray container). The trigger sprayer refers to a dispensing mechanism in which when an operation lever (trigger) is pulled, the liquid contents (cleaning agent composition) in a cylinder is pressurized and pushed out by a plunger (piston) to eject the contents to the outside through a nozzle, and when the trigger is returned, suction is applied in the cylinder by the piston to place the liquid contents in the cylinder. The trigger dispenser is preferably a trigger spray container comprising a mechanism for forming foam (foam-forming mechanism) in addition to the dispensing mechanism described above. The pump dispenser is a container comprising a piston for applying pressure to a liquid and a cylinder, and comprising, at the mouth portion of the container body, a device for dispensing a liquid through a nozzle port by moving the piston, as a dispensing mechanism. The pump dispenser may also comprise the foam-forming mechanism in addition to the dispensing mechanism described above.

The cleaning agent composition of the present invention can be placed in a container having the liquid-dispensing mechanism (e.g., a sensor dispenser, a trigger dispenser, or pump dispenser) or a container having the foam-forming mechanism and the foam-dispensing mechanism (e.g., a sensor dispenser, a trigger dispenser, a pump dispenser, or a squeeze foamer container) according to the desired usage form, i.e., liquid form or foam form. A pump or sensor dispenser is preferable as the container. In particular, deposition, precipitation, and solidification are significantly suppressed in the cleaning agent composition of the present invention, as described above. The cleaning agent composition of the present invention can be thus said to be a cleaning agent composition suitable for sensor dispensers, in which clogging is likely to cause abnormal dispensing.

The cleaning agent composition placed in a container having the foam-dispensing mechanism is dispensed from the container in a state in which foam is formed (in foam form). The dispensed foam cleaning agent composition may be used as is or may be allowed to further foam with, for example, wet hands or a net containing water as necessary. The cleaning agent composition placed in a container having the liquid-dispensing mechanism is dispensed from the container in a liquid state (in liquid form). The dispensed liquid cleaning agent composition may be used as is or may be allowed to foam with, for example, wet hands or a net containing water.

Among the cleaning agent compositions of the present invention, in particular, the cleaning agent composition that has features A, B, C, D, and E-1 has good foamability in addition to good stability at low temperature and good dispensing ability from a container. Thus, with this cleaning agent composition, foam can be easily formed in a container having the foam-forming mechanism or easily formed using hands or a net, and the firmness of formed foam is also excellent. Among the cleaning agent compositions of the present invention, in particular, the cleaning agent composition with a viscosity (measured at 60 rpm and 25° C. with a B-type viscometer for 1 minute, using any rotor) of 100 mPa·s or less, and preferably 50 mPa·s or less, is excellent in not only foamability in a container having the foam-forming mechanism, but also foam dispensing ability from the container. Thus, this cleaning agent composition is preferably placed in a container having the foam-forming mechanism and the foam-dispensing mechanism, and used.

The cleaning agent composition of the present invention can be used as a washing agent for the body, including the hands, feet, and face, such as a hand soap, foot soap, face soap, or body soap; as a washing agent for the hair, such as a shampoo; as a kitchen detergent, such as a dishwashing detergent, a detergent for baby bottles, a detergent for chopping boards, and a detergent for cooking utensils; as a shampoo for pets; or as a laundry detergent for washing a clothing area, such as collars or sleeves of clothes, or for washing clothing in their entirety. Such a washing agent or detergent may be for washing whether with hands, a tool, a dishwasher, or a washing machine.

(II) Method for Improving Storage Stability and/or Dispensing Ability from Dispenser The present invention provides a method for improving storage stability and/or dispensing ability from a dispenser of a cleaning agent composition comprising (a) a fatty acid salt and (b) a sophorose lipid.

The term "storage stability" as used herein means a state in which when the cleaning agent composition is allowed to stand at a low temperature (5±2° C.) and room temperature (25±5° C.) under dark conditions, no precipitation, floating matter, or solid-liquid separation is observed, and the components are homogeneously dissolved or dispersed. When this state persists both at a low temperature and room temperature for at least 1 month, it is determined that the storage stability is extremely good or improved (evaluation: ⊚). When this state persists both at a low temperature and room temperature for at least 1 week, it is determined that the storage stability is good or improved (evaluation: ○). Since the storage stability is also good at a low temperature of 5° C. in both of these cases, it can also be determined that the stability at low temperature is good. On the other hand, when precipitation, floating matter, or solid-liquid separation is observed under conditions either at a low temperature or at room temperature during the time when the composition is allowed to stand for 1 week, it is determined that the storage stability is slightly poor (evaluation: Δ). When precipitation, floating matter, or solid-liquid separation is observed under both conditions, it is determined that the storage stability is poor (evaluation: x).

The phrase "dispensing ability from a dispenser" as used herein means dispensing ability when the cleaning agent composition adjusted to room temperature (25±5° C.) is placed in the storage portions of a pump dispenser and a sensor dispenser that have the dispensing mechanism, and dispensed through their dispensing outlets.

The pump dispenser with a dispensing mechanism for evaluation of dispensing ability is a liquid dispenser (P102

BS; produced by Yoshino Kogyosho Co. Ltd.). In the case in which the dispensing ability of a cleaning agent composition to be evaluated is tested and evaluated by using the pump dispenser according to the method and criteria described in Example 1 later, when the number of times abnormal dispensing occurs is almost the same as that in a positive control (evaluation (○): the number of times abnormal dispensing occurs is in the range of ±2 of the number of times abnormal dispensing occurs in the positive control) or is less than that in the positive control (evaluation (◎): the number of times abnormal dispensing occurs is less than that in the positive control by three or more (≤−3)), it is determined that the dispensing ability from the pump dispenser is good or improved. As the positive control, a liquid (aqueous solution containing about 10% coconut oil potassium soap) obtained by diluting Yashinomi Jun Sekken (product name; produced by Saraya Co., Ltd.) 3-fold with distilled water is used. The series of tests is performed under conditions at room temperature (25±5° C.). The dispensing ability from a pump dispenser may be evaluated by using a pump dispenser having the foam-dispensing mechanism in addition to the above evaluation method. The pump dispenser used in this case is a foam pump (Sueoki Foamer Pump (product name) produced by Yoshino Kogyosho Co. Ltd.; 200/200 mesh).

The sensor dispenser having a dispensing mechanism used for evaluation of dispensing ability is a foam dispensing dispenser (product name: ELEFOAM2.0; produced by Saraya Co., Ltd.; volume: 250 ml). In the case in which the dispensing ability of a cleaning agent composition to be evaluated is tested and evaluated using the sensor dispenser according to the method and criteria described in Examples 12 to 14 later, when the number of times abnormal dispensing occurs is almost the same as that in a positive control (evaluation (◎): the number of times abnormal dispensing occurs is in the range of ±10 of the number of times abnormal dispensing occurs in the positive control) or is not significantly large (evaluation (○): the number of times abnormal dispensing occurs is greater than that in the positive control by more than 10, but not more than 29), it is determined that the dispensing ability from a sensor dispenser is good or improved. Wash Von Medicated Herbal Hand Soap (produced by Saraya Co., Ltd.) is used as the positive control. The series of tests is performed under conditions at room temperature (25±5° C.).

This method can be achieved by setting the proportions of the components of a cleaning agent composition comprising (a) a fatty acid salt and (b) an SL, preferably an acidic SL, in preparing the composition as follows: the proportion of the total amount of the component (a) is 4 to 18 mass % based on the cleaning agent composition taken as 100 mass % (feature A); the proportion of the total amount of one or more fatty acid salts having 12 or fewer carbon atoms is 15 parts by mass or more, and the proportion of the total amount of one or more fatty acid salts having 16 or more carbon atoms is 60 parts by mass or less, based on 100 parts by mass of the total amount of the component (a) (feature B); the proportion of an acidic SL is 80 mass % or more based on the total amount of the component (b) taken as 100 mass % (feature C); and further, the proportion of the total amount of the component (b) is 5 to 80 parts by mass per 100 parts by mass of the total amount of the component (a) (feature D). The pH of the cleaning agent composition is not limited and is preferably adjusted to the range of 9 to 11. A cleaning agent composition comprising the component (a) and the component (b) in which either storage stability or dispensing ability, or both, are improved (good) can be prepared according to this method.

In the method for improving storage stability and/or dispensing ability from a dispenser of the present invention, the types of the components (a) and (b) and the proportions thereof (features A, B, C, and D) are as described in section (I) above, and the descriptions in section (I) above can be incorporated herein by reference. The types of water and one or more optional components other than the components (a) and (b), the amounts thereof, etc. are also as described in section (I) above, and the descriptions in section (I) can be incorporated herein by reference.

(III) Method for Improving Storage Stability, Dispensing Ability from Dispenser, and/or Foamability/Foam Firmness The present invention provides a method for improving storage stability, dispensing ability from a dispenser, and/or foamability/foam firmness of a cleaning agent composition comprising (a) a fatty acid salt and (b) an SL. The phrases "storage stability" and "dispensing ability from a dispenser" are as described in section (II) above.

The phrase "foamability/foam firmness" as used herein can be evaluated by testing a cleaning agent composition adjusted to room temperature (25±5° C.) by the test method described in Example 2 later. In the case in which the composition is tested by the method, it is determined that the foamability/foam firmness is good or improved when the foam height immediately after stirring is 5 mm or more, and the ratio of the foam height after being allowed to stand for 1 minute following stirring to the foam height immediately after stirring (the foam height after being allowed to stand for 1 minute following stirring/the foam height immediately after stirring) is more than ½ (0.5) (evaluation: ○), preferably when the foam height immediately after stirring is 10 mm or more, and the foam height after being allowed to stand for 1 minute following stirring/the foam height immediately after stirring is greater than 0.5 (evaluation: ◎), and more preferably when the foam height immediately after stirring is 10 mm or more, and the foam height after being allowed to stand for 1 minute following stirring/the foam height immediately after stirring is greater than 0.8 (evaluation: •).

This method can be achieved by setting the proportions of the components of a cleaning agent composition comprising (a) a fatty acid salt and (b) an SL, preferably an acidic SL, in preparing the composition as follows: the proportion of the total amount of the component (a) is 4 to 18 mass % based on the cleaning agent composition taken as 100 mass % (feature A); the proportion of the total amount of one or more fatty acid salts having 12 or fewer carbon atoms is 15 parts by mass or more, and the proportion of the total amount of one or more fatty acid salts having 16 or more carbon atoms is 60 parts by mass or less, based on 100 parts by mass of the total amount of the component (a) (feature B); the proportion of an acidic SL is 80 mass % or more based on the total amount of the component (b) taken as 100 mass % (feature C); and further, the proportion of the total amount of the component (b) is 5 to 80 parts by mass per 100 parts by mass of the total amount of the component (a) (feature D), and the proportion of the total amount of the component (b) is 50 parts by mass or less per 100 parts by mass of the total amount of the component (a) (feature E-1). The pH of the cleaning agent composition is not limited and is preferably adjusted to the range of 9 to 11. A cleaning agent composition comprising the component (a) and the component (b) in which either storage stability or dispensing ability, or both, as well as either foamability or foam firmness, or both, are improved (good) can be prepared according to this method.

In the method for improving storage stability, dispensing ability from a dispenser, foamability, and/or foam firmness of the present invention, the types of the components (a) and (b) and the proportions thereof (features A, B, C, D, and E-1) are as described in sections (I) and (II) above, and the descriptions in sections (I) and (II) can be incorporated herein by reference. The types of water and one or more optional components other than the components (a) and (b), the amounts thereof, etc. are also as described in section (I) above, and the descriptions in section (I) can be incorporated herein by reference.

(IV) Method for Improving Storage Stability, Dispensing Ability from Dispenser, Foamability/Foam Firmness, and/or Foam Texture The present invention provides a method for improving storage stability, dispensing ability from a dispenser, foamability, foam firmness, and/or foam texture of a cleaning agent composition comprising (a) a fatty acid salt and (b) an SL. The phrases "storage stability," "dispensing ability from a dispenser," and "foamability/foam firmness" are as described in sections (II) and (III) above.

The phrase "good foam texture" as used herein means that foam that is pleasant to the skin while imparting a comfortable feeling during washing is formed. The phrase "pleasant to the skin" specifically means that when a well-lathering cleaning agent is applied and spread on the palms and backs of the hands and between the fingers, the foam has a fine texture and has appropriate bounciness and softness. Although there is no limitation, this foam texture is a feeling between a feeling common in general facial soaps (a fine, resilient, dense, creamy, doughy, and marshmallow-like feel) and a feeling common in general hand soaps (a slightly rough, fluffy, and soft feel); this foam texture is a finer texture, but is slightly less bouncy and creamy than the feel of facial soaps, thus giving the impression that it has a soft feel and is gentle to the skin. The foam texture can be tested using a cleaning agent composition adjusted to room temperature (25±5° C.) by the method described in Example 5 later (evaluation of feel during use). In the case in which the foam texture is tested by this method, it is determined that the foam texture is significantly good or improved when 9 or more out of 10 panelists evaluate the composition as imparting an excellent feel during use compared with a control (at a significant level of 5% in a paired preference test), and more preferably when 10 out of 10 panelists evaluate the composition as imparting an excellent feel during use compared with the control (at a significant level of 1% in a paired preference test). As the control, a liquid (aqueous solution containing about 104 coconut oil potassium soap) obtained by diluting Yashinomi Jun Sekken (product name; produced by Saraya Co., Ltd.) 3-fold with distilled water is used. The series of tests is performed under conditions at room temperature (25±5° C.).

This method can be achieved by setting the proportions of the components of a cleaning agent composition comprising (a) a fatty acid salt and (b) an SL, preferably an acidic SL, in preparing the composition as follows: the proportion of the total amount of the component (a) is 4 to 18 mass % based on the cleaning agent composition taken as 100 mass % (feature A); the proportion of the total amount of one or more fatty acid salts having 12 or fewer carbon atoms is 15 parts by mass or more, and the proportion of the total amount of one or more fatty acid salts having 16 or more carbon atoms is 60 parts by mass or less, based on 100 parts by mass of the total amount of the component (a) (feature B); the proportion of an acidic SL is 80 mass % or more based on the total amount of the component (b) taken as 100 mass % (feature C); further, the proportion of the total amount of the component (b) is 5 to 80 parts by mass per 100 parts by mass of the total amount of the component (a) (feature D), and the proportion of the total amount of the component (b) is 10 to 50 parts by mass per 100 parts by mass of the total amount of the component (a) (feature E); and based on 100 parts by mass of the total amount of the component (a), the proportion of a lauric acid salt is 15 to 80 parts by mass (feature F-1), the proportion of a myristic acid salt is 10 to 50 parts by mass (feature F-2), the proportion of the total amount of a palmitic acid salt and an oleic acid salt is 5 to 60 parts by mass (feature F-3), and the proportion of fatty acid salts other than lauric acid salts, myristic acid salts, palmitic acid salts, and oleic acid salts is less than 10 parts by mass (feature F-4). The pH of the cleaning agent composition is not limited and is preferably adjusted to the range of 9 to 11. A cleaning agent composition comprising the component (a) and the component (b) in which either storage stability or dispensing ability, or both, either foamability or foam firmness, or both, and foam quality are improved (good) can be prepared according to this method.

In the method for improving storage stability, dispensing ability from a dispenser, foamability, foam firmness, and/or foam texture of the present invention, the types of the components (a) and (b) and the proportions thereof (features A, B, C, D, E-1, E-2, and F-1 to F-4) are as described in sections (I) to (III) above, and the descriptions in sections (I) to (III) can be incorporated herein by reference. The types of water and one or more optional components other than the components (a) and (b), the amounts thereof, etc. are also as described in section (I) above, and the descriptions in section (I) can be incorporated herein by reference.

In the present specification, the terms "comprise" and "contain" encompass the terms "consist essentially of" and "consist of."

EXAMPLES

Examples are given below to illustrate the present invention in more detail. However, in the composition, various modifications may be added without departing from the scope of the present invention; thus, the present invention is not limited to these specific examples. Unless otherwise specified, the step, treatment, or operation in the following experimental examples is performed at room temperature and atmospheric pressure. The room temperature means a temperature in the range of 10 to 40° C.

Reference Production Example 1: Preparation of Sophorose Lipid

A liquid medium containing, per liter, 10 g of aqueous glucose (produced by Nihon Shokuhin Kako Co., Ltd., product name: Nisshoku Gansui Kessho Budoto), 10 g of peptone (produced by Oriental Yeast Co., Ltd., product name: Peptone CB90M), and 5 g of a yeast extract (produced by Asahi Food & Healthcare Co., Ltd., product name: Meast Powder N) was used as a culture medium. *Candida bombicola* ATCC 22214 was cultured in the medium while shaking at 30° C. for two days. This was used as a pre-culture broth.

The pre-culture broth was inoculated into a main culture medium (3 L) in a 5-liter fermenter in an amount of 4%, based on the total amount of the medium, and then cultured at 30° C. at an aeration rate of 0.6 vvm for 6 days for fermentation. The main culture medium contained, per liter, 100 g of aqueous glucose, 50 g of palm olein (produced by NOF Corporation, product name: Palmary 2000), 50 g of oleic acid (produced by Acid Chem, product name: Palmac 760), 1 g of sodium chloride, 10 g of monopotassium phosphate, 10 g of magnesium sulfate heptahydrate, 2.5 g of a yeast extract (produced by Asahi Food & Healthcare Co., Ltd., product name: Meast Powder N), and 1 g of urea (pH of 4.5 to 4.8 before sterilization).

On the 6th day from the start of culturing, the fermentation was stopped. The culture broth removed from the fermenter was heated, then returned to room temperature and allowed to stand for 2 to 3 days. As a result, the culture broth was separated into the following three layers in this order from the bottom: a liquid brown precipitate layer, a milky-white solid layer presumably mainly containing cells, and a supernatant. After the supernatant was removed, industrial water or groundwater was added in an amount equal to the amount of the supernatant removed. While the resulting mixture was stirred, a 48 mass % aqueous sodium hydroxide solution was gradually added to adjust the pH to 6.5 to 6.9, thus solubilizing SLs contained in the culture broth. The resulting product was centrifuged by a tabletop centrifuge (Westfalia: produced by Westfalia Separator AG) to precipitate milky-white solids, and a supernatant was collected. While the collected supernatant was stirred, 62.5 mass % sulfuric acid was gradually added to adjust the pH to 2.5 to 3.0, thus insolubilizing SLs again. After the resulting mixture was allowed to stand for 2 days, the supernatant was removed by decantation as much as possible, thus obtaining the residue as sophorose lipids (SLs) (with a water content of about 50 mass %).

Reference Production Example 2: Preparation of Acidic SL

The SLs (with a water content of about 50 mass %) obtained in the above Reference Production Example 1 were adjusted to a pH of 14 by adding an aqueous sodium hydroxide solution, and the resulting mixture was treated at 80° C. for 2 hours to perform hydrolysis (alkali hydrolysis). Subsequently, the hydrolysate was returned to room temperature, and then adjusted to a pH of 11 by using sulfuric acid (9.8M aqueous solution). The resulting insoluble matter was removed by filtration to obtain a filtrate as an SL-containing aqueous solution. The SL-containing aqueous solution contains an acidic SL in an amount of 30 mass %.

Example 1 and Comparative Examples 1 to 4

(1) Preparation of Cleaning Agent Compositions

Cleaning agent compositions (Example 1 and Comparative Examples 1 to 4) were prepared by mixing the components other than pH adjusters in the proportions shown in Table 2 and finally adjusting the pH of each final composition to near 10 using the pH adjusters. As an SL, the SL-containing aqueous solution (containing 30 mass % acidic SL) prepared in Reference Production Example 2 was used.

TABLE 2

|  |  |  | Example | Comparative Example | | | |
|---|---|---|---|---|---|---|---|
|  |  |  | 1 | 1 | 2 | 3 | 4 |
| Formulation (mass %) | (a) | Potassium caprate C10 | — | — | — | — | — |
|  |  | Potassium laurate C12 | 4.8 | — | 2.4 | — | 14.3 |
|  |  | Potassium myristate C14 | 3.5 | 2.3 | — | — | 3.5 |
|  |  | Potassium palmitate C16 | — | 1.4 | 4.6 | — | 2.3 |
|  |  | Potassium oleate C18 | 3.6 | — | 0.3 | — | 1.1 |
|  |  | Potassium cocoate | — | — | — | 3.0 | — |
|  | (b) | SL-containing aqueous solution (30 mass %) | 30 | 6.7 | 4.0 | 8.3 | 10 |
|  | Humectant | Glycerin | 0 | — | — | 4 | 2 |
|  |  | Butylene glycol | 4 | — | — | — | — |
|  |  | Propanediol | — | — | 4 | — | 4 |
|  | Other components | Potassium hydroxide (pH adjuster) | Appropriate amount | Appropriate amount | Appropriate amount | Appropriate amount | Appropriate amount |
|  |  | Citric acid (pH adjuster) | Appropriate amount | Appropriate amount | Appropriate amount | Appropriate amount | Appropriate amount |
|  |  | Perfume (including essential oil) | — | 0.08 | — | 0.1 | 0.05 |
|  |  | Edetic acid salt (chelating agents) | — | — | — | 0.1 | — |
|  | Solvent | Distilled water | Balance | Balance | Balance | Balance | Balance |
|  |  | Total (mass %) | 100 | 100 | 100 | 100 | 100 |
| Relationship with claims | A: (a) Total of fatty acid salts |  | 11.9 | 3.7 | 7.3 | 3.0 | 21.2 |
|  | B: Proportion of fatty acid salt having 12 or fewer carbon atoms |  | 40.3 | 0 | 32.8 | 64.0 | 67.4 |
|  | B: Proportion of fatty acid salt having 16 or more carbon atoms |  | 30.2 | 37.8 | 67.1 | 18.8 | 16.0 |
|  | C: Proportion of acidic SL in component (b) (100 mass %) |  | 100 | 100 | 100 | 100.0 | 100 |
|  | D: Proportion of component (b) per 100 parts by mass of component (a) |  | 75.6 | 54.3 | 16.4 | 83.0 | 14.1 |
| Evaluation | Storage stability |  | ◎ | X | X | Δ | ◎ |
|  | Dispensing ability (foam pump) |  | ○ | X | X | ○ | Δ |
|  | Dispensing ability (liquid pump) |  | ○ | X | X | ○ | Δ |

(2) Test Methods (Evaluation of Storage Stability and Dispensing Ability)

The cleaning agent compositions prepared as described above (Example 1 and Comparative Examples 1 to 4) were used as samples and evaluated for their storage stability and dispensing ability from pump dispensers (liquid-dispensing pump dispenser and foam-dispensing pump dispenser) according to the following methods.

(i) Storage Stability

Each of the cleaning agent compositions (Example 1 and Comparative Examples 1 to 4) was individually divided into two groups, i.e., a sample for storage at 5° C. and a sample for storage at room temperature, and each sample was individually placed in a PET container (50 ml). The samples for storage at 5° C. of the cleaning agent compositions (Example 1 and Comparative Examples 1 to 4) were allowed to stand under conditions at 5° C.±2° C. (in the dark), and the samples for storage at room temperature of the compositions were allowed to stand under conditions at room temperature (25±5° C.) (in the dark). Subsequently, the appearance immediately after storage was observed visually, and the storage stability was evaluated based on the following criteria.

Criteria for Evaluating Storage Stability

◎: During a 1-month storage period, no precipitation, floating matter, or solid-liquid separation was observed in the sample for storage at 5° C. or the sample for storage at room temperature, and the components were homogeneously dissolved or dispersed in both the sample for storage at 5° C. and the sample for storage at room temperature.

○: During a 1-week storage period, no precipitation, floating matter, or solid-liquid separation was observed in the sample for storage at 5° C. or the sample for storage at room temperature, and the components were homogeneously dissolved or dispersed in both the sample for storage at 5° C. and the sample for storage at room temperature.

Δ: During a 1-week storage period, precipitation, floating matter, or solid-liquid separation was observed in either the sample for storage at 5° C. or the sample for storage at room temperature.

x: During a 1-week storage period, precipitation, floating matter, or solid-liquid separation was observed in both the sample for storage at 5° C. and the sample for storage at room temperature.

(ii) Dispensing Ability

Each of the cleaning agent compositions (Example 1 and Comparative Examples 1 to 4) was individually divided into two groups, i.e., a sample for foam dispenser and a sample for liquid dispenser. Each sample for foam was individually placed in a foam (foam-dispensing) pump dispenser, which is a dispenser from which foam is dispensed after liquid is mixed with air (Sueoki Foamer Pump (product name) produced by Yoshino Kogyosho Co., Ltd.; 200/200 mesh; volume: 300 ml)(the same applies hereinafter). Each sample for liquid was individually placed in a liquid (liquid-dispensing) pump dispenser, which is a dispenser from which liquid is dispensed (P102 BS; produced by Yoshino Kogyosho Co. Ltd.; volume: 250 ml)(the same applies hereinafter). A dispensing test was performed once a day (in principle, Monday to Friday, except for Saturdays, Sundays, and national holidays) for a total of 20 days, in a state in which each cleaning agent composition placed in the pump dispenser was adjusted to room temperature (25±5° C.) (total number of dispenses: 20). The dispensing test was performed as follows: when each cleaning agent composition immediately after preparation was dispensed through the dispensing outlet of the pump dispenser (first time), whether there was abnormal dispensing (clogging in dispensing, or dispensing in an unexpected direction) was checked; if there was no abnormal dispensing, the cleaning agent composition immediately after preparation was dispensed through the dispensing outlet of the pump dispenser placed on a laboratory table, and a circle with a radius of 3 cm was drawn around the point of the laboratory table on which the composition fell; and during the test period, whether the dispensed liquid (dispensed foam) fell within the circle at all times, and the presence or absence of clogging in dispensing were checked. As a positive control sample (positive control), a liquid (aqueous solution containing about 10% coconut oil potassium soap) obtained by diluting Yashinomi Jun Sekken (product name; produced by Saraya Co., Ltd.) 3-fold with distilled water was used and placed in a foam pump dispenser and a liquid pump dispenser in the same manner as above, and the dispensing test was performed in the same manner as above.

The dispensing test was performed for a total of 20 days (total number of dispenses: 20), and the number of times abnormal dispensing (clogging in dispensing, abnormality in the dispensing direction) occurred was recorded, and the dispensing ability was evaluated from the total number of times abnormal dispensing occurred based on the following criteria.

Criteria for Evaluating Dispensing Ability

◎: The number of times abnormal dispensing occurred was less than that in the positive control by three or more (≤−3).

○: The number of times abnormal dispensing occurred was within ±2 of the number of times abnormal dispensing occurred in the positive control.

Δ: The number of times abnormal dispensing occurred was greater than that in the positive control by three or more (≥3)

x: The composition could not be favorably dispensed from the pump dispenser from the first dispensing.

(3) Test Results

Table 2 shows the results.

Examples 2 to 4

(1) Preparation of Cleaning Agent Compositions

Cleaning agent compositions were prepared by mixing the components other than pH adjusters in the proportions shown in Table 3 and finally adjusting the pH of each final composition to near 10 using the pH adjusters (Examples 2 to 4).

TABLE 3

|  |  | Example | | |
|  |  | 2 | 3 | 4 |
| --- | --- | --- | --- | --- |
| Formulation (a) (mass %) | Potassium caprate C10 | — | 1.2 | — |
|  | Potassium laurate C12 | 3.8 | 8.9 | — |
|  | Potassium myristate C14 | 0.5 | 1.7 | — |
|  | Potassium palmitate C16 | 0.1 | — | — |

TABLE 3-continued

|  |  |  | Example 2 | Example 3 | Example 4 |
|---|---|---|---|---|---|
|  |  | Potassium oleate C18 | — | — | — |
|  |  | Potassium cocoate | — | — | 6.3 |
|  | (b) | SL-containing aqueous solution (30 mass %) | 2.1 | 14 | 4.6 |
|  | Humectant | Glycerin | 10 | 5 | 3 |
|  |  | Butylene glycol | — | 1 | 4 |
|  | Other components suitably added | Carbomer (thickener) | — | — | 0.3 |
|  |  | Potassium hydroxide (pH adjuster) | Appropriate amount | Appropriate amount | Appropriate amount |
|  |  | Citric acid (pH adjuster) | Appropriate amount | Appropriate amount | Appropriate amount |
|  |  | Perfume (including essential oil) | 0.2 | 0.1 | 0.05 |
|  |  | Edetic acid salt (chelating agent) | — | — | 0.1 |
|  | Solvent | Distilled water | Balance | Balance | Balance |
|  | Total (mass %) |  | 100 | 100 | 100 |
| Relationship with claims | A: (a) Total of fatty acid salts |  | 4.4 | 11.8 | 6.3 |
|  | B: Proportion of fatty acid salt having 12 or fewer carbon atoms |  | 86.3 | 85.5 | 64.0 |
|  | B: Proportion of fatty acid salt having 16 or more carbon atoms |  | 2.2 | 0 | 18.8 |
|  | C: Proportion or acidic SL in component (b) (100 mass %) |  | 100 | 100 | 100 |
|  | D: Proportion of component (b) per 100 parts by mass of component (a) |  | 14.3 | 35.5 | 21.9 |
|  | E: Proportion of component (b) per 100 parts by mass of component (a) |  | 14.3 | 35.5 | 21.9 |
| Evaluation | Storage stability |  | ◎ | ◎ | ○ |
|  | Dispensing ability |  | ◎ | ◎ | ○ |
|  | Foamability/foam firmness |  | ◎ | ◎ | ○ |

(2) Test Methods (Evaluation of Storage Stability, Dispensing Ability, and Foamability/Foam Firmness)

The cleaning agent compositions prepared as described above (Examples 2 to 4) were used as samples and evaluated for their storage stability and dispensing ability from a pump dispenser according to the method explained in Example 1 above. The foamability and foam firmness were evaluated according to the following method.

(iii) Foamability/Foam Firmness 2.5 ml of each of the samples (Examples 2 to 4) and 2.5 ml of tap water (hardness: about 80 mg/l) were individually placed in a test tube (18 mm in diameter×180 mm in length) and stirred with a vortex mixer (UZUSIO VTX-3000L MIXER; LHS) for 20 seconds. The amount of bubbles (the length from the liquid surface to the top of bubbles in the test tube ("foam height")) of each sample was measured immediately after stirring and after being allowed to stand for 1 minute following stirring. The test was performed under conditions at room temperature while adjusting the temperature of each sample to room temperature (25±5° C.).

The foamability and foam firmness of each of the samples (Examples 2 to 4) were evaluated according to the following criteria.

Criteria for Evaluating Foamability and Foam Firmness

●: The foam height immediately after stirring was 10 mm or more, and the ratio of the foam height after being allowed to stand for 1 minute following stirring to the foam height immediately after stirring was >0.8

◎: The foam height immediately after stirring was 10 mm or more, and the ratio of the foam height after being allowed to stand for 1 minute following stirring to the foam height immediately after stirring was >0.5

○: The foam height immediately after stirring was 5 mm or more, and the ratio of the foam height after being allowed to stand for 1 minute following stirring to the foam height immediately after stirring was >0.5

Δ: The foam height immediately after stirring was 5 mm or more, and the ratio of the foam height after being allowed to stand for 1 minute following stirring to the foam height immediately after stirring was <0.5 x: The foam height immediately after stirring was less than 5 mm.

(3) Results

Table 3 shows the results. Table 3 shows liquid dispensing ability from a liquid pump dispenser. The foam dispensing ability from a foam pump dispenser was also good (○) (Examples 2 and 3).

Examples 5 to 11

(1) Preparation of Cleaning Agent Compositions

Cleaning agent compositions were prepared by mixing the components other than pH adjusters in the proportions shown in Table 4 and finally adjusting the pH of each final composition to near 10 using the pH adjusters (Examples 5 to 11).

TABLE 4

|  |  |  | Example 5 | 6 | 7 | 8 | 9 | 10 | 11 |
|---|---|---|---|---|---|---|---|---|---|
| Formulation (mass %) | (a) | Potassium caprate C10 | — | — | — | — | — | — | — |
|  |  | Potassium laurate C12 | 6.0 | 2.4 | 3.6 | 42 | 8.7 | 9.5 | 4.8 |
|  |  | Potassium myristate C14 | 1.5 | 3.5 | 1.2 | 3.5 | 3.1 | 2.9 | 1.7 |

TABLE 4-continued

| | | | Example | | | | | | |
|---|---|---|---|---|---|---|---|---|---|
| | | | 5 | 6 | 7 | 8 | 9 | 10 | 11 |
| | | Potassium palmitate C16 | 0.9 | 0.9 | 0.7 | 1.1 | 1.5 | 1.7 | — |
| | | Potassium oleate C18 | — | 5.7 | — | — | 0.8 | 3.4 | 8.0 |
| | (b) | SL-containing aqueous solution (30 mass %) | 3.5 | 7.0 | 5.0 | 6.7 | 9.0 | 16 | 6.0 |
| | Humectant | Glycerin | 8 | 4 | 3 | 5 | 15 | 4 | 8 |
| | | Butylene glycol | — | — | — | — | — | 4 | 1 |
| | | Propanediol | — | 3 | — | — | — | — | 1 |
| | Other components | Carbomer (thickener) | — | — | 0.5 | — | — | — | — |
| | | Potassium hydroxide (pH adjuster) | Appropriate amount | Appropriate amount | Appropriate amount | Appropriate amount | Appropriate amount | Appropriate amount | Appropriate amount |
| | | Citric acid (pH adjuster) | Appropriate amount | Appropriate amount | Appropriate amount | Appropriate amount | Appropriate amount | Appropriate amount | Appropriate amount |
| | | Perfume (including essential oil) | — | — | 0.1 | 0.08 | — | 0.2 | 0.1 |
| | Solvent | Distilled water | Balance | Balance | Balance | Balance | Balance | Balance | Balance |
| | Total (mass %) | | 100 | 100 | 100 | 100 | 100 | 100 | 100 |
| Relationship with claims | A: (a) Total of fatty acid salts | | 8.4 | 12.5 | 5.5 | 8.8 | 14.1 | 17.5 | 14.5 |
| | B: Proportion of fatty acid salt having 12 or fewer carbon atoms | | 71.4 | 19.2 | 65.4 | 47.7 | 61.7 | 54.2 | 33.1 |
| | B: Proportion of fatty acid salt having 16 or more carbon atoms | | 10.7 | 52.8 | 12.7 | 12.5 | 16.3 | 29.1 | 55.1 |
| | C: Proportion of acidic SL in component (b) (100 mass %) | | 100 | 100 | 100 | 100 | 100 | 100 | 100 |
| | D: Proportion of component (b) per 100 parts by mass of component (a) | | 12.5 | 16.8 | 27.2 | 22.8 | 191 | 27.4 | 12.4 |
| | E: Proportion of component (b) per 100 parts by mass of component (a) | | 12.5 | 16.8 | 27.2 | 22.8 | 19.1 | 27.4 | 12.4 |
| | F-1: Proportion of lauric acid salt based on 100 parts by mass of component (a) | | 71.4 | 19.2 | 65.4 | 47.4 | 61.7 | 54.2 | 33.1 |
| | F-2: Proportion of myristic acid salt based on 100 parts by mass of component (a) | | 17.8 | 28.0 | 21.8 | 39.7 | 21.9 | 16.5 | 11.7 |
| | F-3: Proportion of palmitic acid salt and oleic acid salt based on 100 parts by mass of component (a) | | 10.7 | 528 | 12.7 | 12.5 | 16.3 | 29.1 | 55.1 |
| | F-4: Proportion of other fatty acid salts based on 100 parts by mass of component (a) | | 0 | 0 | 0 | 0 | 0 | 0 | 0 |
| Evaluation | Storage stability | | ○ | ○ | ○ | ○ | ◎ | ◎ | ◎ |
| | Dispensing ability | | ◎ | ○ | ◎ | ◎ | ○ | ○ | ○ |
| | Foamability/foam firmness | | ◎ | ● | ● | ◎ | ● | ○ | ○ |
| | Feel during use | | ◎ | ○ | ◎ | ○ | ◎ | ◎ | ○ |

(2) Test Methods (Evaluation of Storage Stability, Dispensing Ability, Foamability/Foam Firmness, and Foam Texture)

The cleaning agent compositions prepared as described above (Examples 5 to 11) were used as samples and evaluated for their storage stability, dispensing ability from a dispenser, foamability, and foam firmness according to the methods explained in Examples 1 and 2 to 4 above. The foam texture was evaluated by the following method.

(iv) Foam Texture

Each of the samples (Examples 5 to 11) was individually divided into two groups, i.e., a sample for foam dispenser and a sample for liquid dispenser. Each sample for foam was individually placed in a foam pump dispenser (volume: 300 ml), and each sample for liquid was individually placed in a liquid pump dispenser (volume: 250 ml). Expert panelists used the cleaning agent compositions (Examples 5 to 11) placed in the pump dispensers according to the following method, and evaluated the foam texture based on feel during use. In the test, a liquid (aqueous solution containing about 10% coconut oil potassium soap) obtained by diluting Yashinomi Jun Sekken (product name; produced by Saraya Co., Ltd.) 3-fold with distilled water was used as a control sample (control example) and placed in a foam pump dispenser (volume: 300 ml) and a liquid pump dispenser (volume: 250 ml) in the same manner as above, and the foam texture was evaluated in the same manner as above. The test was performed at room temperature.

(1) Use of Liquid Pump Dispenser

Ten expert panelists wetted their hands with water, and each of the samples (Examples 5 to 11 and the control example) was individually applied to the wet hands from the liquid pump dispenser in an amount of one push (1 ml) and lathered well for 30 seconds. The foam was rubbed all over the hands, including on the backs of the hands, and on the wrists. The feel during use was evaluated by checking whether the foam quality was good (whether the foam has a fine texture and appropriate bounciness and softness, is pleasant to the skin while imparting a comfortable feeling during washing, and is gentle and comfortable to the skin) compared with the foam of the control example based on the following criteria.

Criteria for Evaluating Feel During Use

⊚: 10 out of the 10 panelists evaluated the foam quality as being good compared with the control example (at a significant level of 1% in the paired preference test)

○: 9 out of the 10 panelists evaluated the foam quality as being good compared with the control example (at a significant level of 5% in the paired preference test).

Δ: 8 or less out of the 10 panelists evaluated the foam quality as being good compared with the control example (at a significant level of 5% in the paired preference test).

x: At least 8 out of the 10 panelists evaluated the foam quality of the control example as being superior (at a significant level of 5% by the paired preference test)

(2) Use of Foam Pump Dispenser

Ten expert panelists wetted their hands with water, and each of the samples (Examples 5 to 11 and the control example) was individually applied to the wet hands from the foam pump dispenser in an amount of two pushes (2 ml) and lathered well for 30 seconds. The foam was rubbed all over the hands, including on the backs of the hands, between the fingers, and on the wrists. The feel during use was evaluated by checking whether the feel during use was excellent (whether the foam imparted a feeling of softness, rather than a creamy feel, and was gentle and comfortable) compared with the foam of the control example based on the following criteria.

Criteria for Evaluating Feel During Use

⊚: 10 out of the 10 panelists evaluated the feel during use as being excellent compared with the control example (at a significant level of 1% in the paired preference test).

○: 9 out of the 10 panelists evaluated the feel during use as being excellent compared with the control example (at a significant level of 5% in the paired preference test).

Δ: 8 or less out of the 10 panelists evaluated the feel during use as being excellent compared with the control example (at a significant level of 5% in the paired preference test).

x: At least 8 out of the 10 panelists evaluated the feel during use in the control example as being superior (at a significant level of 5% in the paired preference test).

(3) Results

Table 4 shows the results. Table 4 shows dispensing ability and a feel during use when the liquid pump dispenser was used. The dispensing ability from the foam pump dispenser and the feel during use were also good (○ and ⊚) (Examples 5, 6, and 8 to 11).

The results of Examples 1 to 11 show that a cleaning agent that exhibits improved storage stability, especially stability at low temperature, which is an object of soaps, exhibits improved dispensing ability from a pump dispenser, and is less likely to cause defective dispensing can be prepared by adjusting the proportions of the components in a cleaning agent composition comprising (a) one or more fatty acid salt and (b) an SL, especially an acidic SL, so that the proportion of the total amount of the component (a) is 4 to 18 mass % based on the cleaning agent composition taken as 100 mass %, and the proportion of the total amount of the fatty acid salt having 12 or fewer carbon atoms is 15 parts by mass or more, and the proportion of the total amount of fatty acid salt having 16 or more carbon atoms is 60 parts by mass or less, based on 100 parts by mass of the component (a).

The results of Examples 2 to 11 show that a cleaning agent that exhibits good storage stability and improved dispensing ability from a pump dispenser, as well as good foamability and foam firmness, can be prepared by setting the proportion of the component (b) to be 50 parts by mass or less per 100 parts by mass of the component (a) in addition to setting the above proportions.

Further, the results of Examples 5 to 11 show that a cleaning agent that ensures good foam quality and an excellent feel during use in addition to the above properties can be prepared by setting, in addition to setting the above proportions, the proportion of the component (b) to 10 parts by mass or more per 100 parts by mass of the component (a) and adjusting the proportions of the following components so that based on 100 parts by mass of the component (a), the proportion of a lauric acid salt is 20 to 80 parts by mass, the proportion of a myristic acid salt is 10 to 50 parts by mass, the proportion of the total amount of a palmitic acid salt and an oleic acid salt is 5 to 60 parts by mass, and the proportion of other fatty acid salts is less than 10 parts by mass.

Examples 12 to 14 and Comparative Examples 5 and 6

(1) Preparation of Cleaning Agent Compositions

Cleaning agent compositions were prepared by mixing the components other than pH adjusters in the proportions shown in Table 5 and finally adjusting the pH of each final composition to near 10 using the pH adjusters (Examples 12 to 14 and Comparative Examples 5 and 6). As SLs, a lactonic SL (1',4''-Sophorolactone 6',6''-diacetate; produced by Cayman Chemical) and the SL-containing aqueous solution (containing 30 mass % acidic SL) prepared in Reference Production Example 2 were used.

TABLE 5

|   |   |   | Example | | | Comparative Example | |
|---|---|---|---|---|---|---|---|
|   |   |   | 12 | 13 | 14 | 5 | 6 |
| Formulation (mass %) | (a) | Potassium cocoate | 10 | 10 | 10 | 10 | 10 |
|   | (b) | SL-containing aqueous solution (30 mass %) | 3.0 | 5.0 | 17 | 19.3 | 1.0 |
|   |   | Lactonic SL | 0 | 0.1 | 1.2 | 2.3 | 0 |
|   | Humectant | Glycerin | 10 | 10 | 10 | 10 | 10 |
|   | Other components | Potassium hydroxide | pH adjustment | pH adjustment | pH adjustment | pH adjustment | pH adjustment |

TABLE 5-continued

| | | | Example | | | Comparative Example | |
|---|---|---|---|---|---|---|---|
| | | | 12 | 13 | 14 | 5 | 6 |
| | | Citric acid | pH adjustment | pH adjustment | pH adjustment | pH adjustment | pH adjustment |
| | | Perfume including essential oil) | 0.1 | 0.1 | 0.1 | 0.1 | 0.1 |
| | Solvent | Distilled water | Balance | Balance | Balance | Balance | Balance |
| Relationship with claims | A: (a) Total of fatty acid salts | | 10 | 10 | 10 | 10 | 10 |
| | B: Proportion of fatty acid salt having 12 or fewer carbon atoms | | 64.0 | 64.0 | 64.0 | 64.0 | 64.0 |
| | B: Proportion of fatty acid salt having 16 or more carbon atoms | | 18.8 | 18.8 | 18.8 | 18.8 | 18.8 |
| | C: Proportion of acidic SL in component (b) (100 mass %) | | 100 | 93.7 | 80.9 | 71.5 | 100 |
| | D: Proportion of component (b) per 100 parts by mass of component (a) | | 9.0 | 16.0 | 63.0 | 80.9 | 3.0 |
| Evaluation | | Storage stability | ○ | ○ | ○ | ○ | ○ |
| | | Dispensing ability (sensor type) | ◎ | ◎ | ○ | X | X |

(2) Test Methods (Evaluation of Storage Stability and Dispensing Ability)

The cleaning agent compositions prepared as described above (Examples 12 to 14 and Comparative Examples 5 and 6) were used as samples, and the storage stability and dispensing ability from a sensor dispenser were evaluated according to the following methods.

(i) Storage Stability

Each of the cleaning agent compositions (Examples 12 to 14 and Comparative Examples 5 and 6) was individually divided into two groups, i.e., a sample for storage at 5° C. and a sample for storage at room temperature, and each sample was individually placed in a PET container (50 ml). The samples for storage at 5° C. of the cleaning agent compositions were allowed to stand under conditions at 5° C.±2° C. (in the dark), and the samples for storage at room temperature of the compositions were allowed to stand under conditions at room temperature (25±5° C.) (in the dark). Subsequently, the appearance immediately after storage was observed visually, and the storage stability was evaluated based on the same criteria as in Example 1.

(ii) Dispensing Ability from Sensor Dispenser

Each of the cleaning agent compositions (Examples 12 to 14 and Comparative Examples 5 and 6) was individually placed in a foam-dispensing sensor dispenser (product name: ELEFOAM2.0; produced by Saraya Co., Ltd.; volume: 250 ml). A dispensing test was performed once a day (in principle, Monday to Friday, except for Saturdays, Sundays, and national holidays) for a total of 60 days, in a state in which each cleaning agent composition individually placed in the sensor dispenser was adjusted to room temperature (25±5° C.) (total number of dispenses: 60). The dispensing test was performed as follows: each cleaning agent composition immediately after preparation was dispensed through the dispensing outlet of the sensor dispenser placed on a laboratory table; a circle with a radius of 3 cm was drawn around the point of the laboratory table on which the composition fell; and during the test period, whether the dispensed liquid (dispensed foam) fell within the circle at all times, and the presence or absence of dispensing were checked. As a positive control sample (positive control), Wash Von Medicated Herbal Hand Soap (produced by Saraya Co., Ltd.), which is a cleaning agent suited to the sensor dispenser described above, was used and placed in the sensor dispenser in the same manner as above, and the dispensing test was performed in the same manner as above.

The dispensing test was performed for a total of 60 days (total number of dispenses: 60), and the number of times abnormal dispensing (the presence or absence of dispensing, abnormality in the dispensing direction) occurred was recorded, and the dispensing ability was evaluated from the total number of times abnormal dispensing occurred based on the following criteria.

Criteria for Evaluating Dispensing Ability

◎: The number of times abnormal dispensing occurred was within ±+10 of the number of times abnormal dispensing occurred in the positive control.

○: The number of times abnormal dispensing occurred was greater than that in the positive control by more than 10, but not more than 29.

Δ: The number of times abnormal dispensing occurred was greater than that in the positive control by 30 or more.

x: Dispensing the composition became impossible at any point in time during the test period.

(3) Test Results

Table 5 shows the results.

The cleaning agent composition of Example 12 differs from the cleaning agent composition of Comparative Example 6 in that the proportion of (b) the SL is 9 parts by mass in Example 12 and is 3 parts by mass in Comparative Example 6, per 100 parts by mass of (a) the fatty acid salt. Due to this difference, the dispensing ability from the sensor dispenser was extremely good in Example 12. The cleaning agent compositions of Examples 13 and 14 differ from those of Comparative Examples 5 and 6 in that the proportion of the component (b) is 16 parts by mass in Example 13 and is 63 parts by mass in Example 14, per 100 parts by mass of the component (a), whereas the proportion of the component (b) is 81 parts by mass in Comparative Example 5 and is 3 parts by mass in Comparative Example 6, per 100 parts by mass of the component (a). The dispensing ability from the sensor dispenser was extremely good in Examples 13 and 14. The cleaning agent compositions of Examples 13 and 14 contained a lactonic SL in addition to an acidic SL; however, the proportion of the acidic SL was as large as 93.7 mass % and 80.9 mass %, respectively, based on the total amount of the SLs taken as 100 mass %. The cleaning agent compositions of Examples 13 and 14 exhibited good dispensing ability from a sensor dispenser in addition to good storage stability. In contrast, the pH of the cleaning agent composition of Comparative Example 5 decreased over time, and a fine precipitate was observed at room temperature 1 week after the composition of Comparative Example 5 was prepared and allowed to stand. The interior or dispensing outlet of the sensor dispenser is clogged with such a precipitate, which makes it impossible to dispense the composition. In the dispensing test of the cleaning agent composition of Comparative Example 6, liquid remaining inside the pump or at the tip of the dispensing outlet evaporated and stuck to the interior or dispensing outlet of the sensor dispenser, causing more abnormalities in dispensing than the positive control.

The results show that in the case of the cleaning agent composition that is to be placed in a sensor dispenser and used, it is preferable to adjust the proportion of (b) the SL to the range of 5 to 80 parts by mass, preferably 5 to 70 parts by mass, and more preferably 8 to 60 parts by mass, per 100 parts by mass of (a) the fatty acid salt, from the viewpoint of storage stability and dispensing ability from a sensor dispenser. The results also show that when the cleaning agent composition contains a lactonic SL in addition to an acidic SL as an SL, it is preferable to set the proportion of the acidic SL in the total amount of the SLs to 80 mass % or more from the viewpoint of storage stability and dispensing ability from a sensor dispenser.

INDUSTRIAL APPLICABILITY

Since the cleaning agent composition of the present invention is excellent in storage stability, especially stability at low temperature, and exhibits good dispensing ability from a dispenser, it can be stored in a sensor dispenser, trigger dispenser, or pump dispenser and used daily for washing, for example, the body (e.g., hands, face, body, and hair) and dishes. The cleaning agent composition of the present invention has, in addition to the above properties, good foamability/foam firmness and/or enables formation of foam that is pleasant to the skin while imparting a comfortable feeling during washing. Thus, the cleaning agent composition of the present invention can be used comfortably every day.

The invention claimed is:

1. A cleaning agent composition comprising (a) at least one fatty acid salt (excluding triethanolamine salts of fatty acids), (b) a sophorose lipid, and (c) a pH adjuster, wherein
   A) the proportion of the total amount of the component (a) is 4 to 18 mass % based on the cleaning agent composition taken as 100 mass %;
   B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
   C) the proportion of an acidic sophorose lipid is 80 mass % or more based on the total amount of the component (b) taken as 100 mass %;
   D) the proportion of the total amount of the component (b) is 5 to 80 parts by mass per 100 parts by mass of the total amount of the component (a); and
   E) the composition has a pH in the range of 9 to 11.

2. The cleaning agent composition according to claim 1, wherein (a) the at least one fatty acid salt comprises salts of two or more fatty acids selected from the group consisting of $C_{8-22}$ saturated fatty acids and unsaturated fatty acids.

3. The cleaning agent composition according to claim 1, wherein (a) the at least one fatty acid salt is a salt of at least one fatty acid selected from the group consisting of capric acid, lauric acid, myristic acid, palmitic acid, oleic acid, coconut oil fatty acid, and palm kernel fatty acid.

4. The cleaning agent composition according to claim 1, wherein the proportion of an acidic sophorose lipid is 100 mass % based on the total amount of the component (b) taken as 100 mass %.

5. The cleaning agent composition according to claim 1, wherein
   F) the proportion of the total amount of the component (b) is 50 parts by mass or less per 100 parts by mass of the total amount of the component (a).

6. The cleaning agent composition according to claim 5, wherein
   F) the proportion of the total amount of the component (b) is 10 parts by mass or more per 100 parts by mass of the total amount of the component (a); and
   G) based on 100 parts by mass of the total amount of the component (a),
      G-1) the proportion of a lauric acid salt is 15 to 80 parts by mass,
      G-2) the proportion of a myristic acid salt is 10 to 50 parts by mass,
      G-3) the proportion of the total amount of a palmitic acid salt and an oleic acid salt is 5 to 60 parts by mass, and
      G-4) the proportion of the total amount of fatty acid salts other than lauric acid salts, myristic acid salts, palmitic acid salts, and oleic acid salts is less than 10 parts by mass.

7. A cleaning agent composition for dispensers in which the cleaning agent composition according to claim 1 is placed in the storage portion of a container comprising a storage portion and a dispensing portion that comprises a dispensing mechanism.

8. The cleaning agent composition for dispensers according to claim 7, wherein the container comprising a storage portion and a dispensing portion that comprises a dispensing mechanism is a dispenser comprising a dispensing portion that comprises a liquid-dispensing mechanism or a dispenser comprising a dispensing portion that comprises a foam-forming mechanism and a foam-dispensing mechanism.

9. The cleaning agent composition for dispensers according to claim 7, wherein the container comprising a storage portion and a dispensing portion that comprises a dispensing mechanism is an auto-dispenser comprising a mechanism for automatically dispensing contents to the outside with a sensor.

10. A method for improving storage stability and/or dispensing ability from a dispenser of a cleaning agent composition comprising (a) at least one fatty acid salt (excluding triethanolamine salts of fatty acids), (b) a sophorose lipid, and (c) a pH adjuster, the method comprising preparing the composition such that
   A) the proportion of the total amount of the component (a) is 4 to 18 mass % based on the cleaning agent composition taken as 100 mass %;
   B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
   C) the proportion of an acidic sophorose lipid is 80 mass % or more based on the total amount of the component (b) taken as 100 mass %;
   D) the proportion of the total amount of the component (b) is 5 to 80 parts by mass per 100 parts by mass of the total amount of the component (a); and
   E) the composition has a pH in the range of 9 to 11.

11. The method according to claim 10, wherein (a) the at least one fatty acid salt comprises salts of two or more fatty acids selected from the group consisting of $C_{8-22}$ saturated fatty acids and unsaturated fatty acids.

12. A method for improving storage stability, dispensing ability from a dispenser, foamability, and/or foam firmness of a cleaning agent composition comprising (a) at least one fatty acid salt (excluding triethanolamine salts of fatty acids), (b) a sophorose lipid, and (c) a pH adjuster, the method comprising preparing the composition such that A) the proportion of the total amount of the component (a) is 4 to 18 mass % based on the cleaning agent composition taken as 100 mass %;
B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
C) the proportion of an acidic sophorose lipid is 80 mass % or more based on the total amount of the component (b) taken as 100 mass %;
D) the proportion of the total amount of the component (b) is 5 to 80 parts by mass per 100 parts by mass of the total amount of the component (a);
E) the composition has a pH in the range of 9 to 11; and
F) the proportion of the total amount of the component (b) is 50 parts by mass or less per 100 parts by mass of the total amount of the component (a).

13. The method according to claim 12, wherein (a) the at least one fatty acid salt comprises salts of two or more fatty acids selected from the group consisting of $C_{8-22}$ saturated fatty acids and unsaturated fatty acids.

14. A method for improving storage stability, dispensing ability from a dispenser, foamability, foam firmness, and/or foam texture of a cleaning agent composition comprising (a) at least one fatty acid salt (excluding triethanolamine salts of fatty acids), (b) a sophorose lipid, and (c) a pH adjuster, the method comprising preparing the composition such that A) the proportion of the total amount of the component (a) is 4 to 18 mass % based on the cleaning agent composition taken as 100 mass %;
B) the proportion of the total amount of a fatty acid salt having 12 or fewer carbon atoms is 15 parts by mass or more, and the proportion of the total amount of a fatty acid salt having 16 or more carbon atoms is 60 parts by mass or less, based on 100 parts by mass of the total amount of the component (a);
C) the proportion of an acidic sophorose lipid is 80 mass % or more based on the total amount of the component (b) taken as 100 mass %;
D) the proportion of the total amount of the component (b) is 5 to 80 parts by mass per 100 parts by mass of the total amount of the component (a);
E) the composition has a pH in the range of 9 to 11;
F) the proportion of the total amount of the component (b) is 10 to 50 parts by mass per 100 parts by mass of the total amount of the component (a); and
G) based on 100 parts by mass of the total amount of the component (a),
G-1) the proportion of a lauric acid salt is 15 to 80 parts by mass,
G-2) the proportion of a myristic acid salt is 10 to 50 parts by mass,
G-3) the proportion of the total amount of a palmitic acid salt and an oleic acid salt is 5 to 60 parts by mass, and
G-4) the proportion of the total amount of fatty acid salts other than lauric acid salts, myristic acid salts, palmitic acid salts, and oleic acid salts is less than 10 parts by mass.

15. The method according to claim 14, wherein (a) the at least one fatty acid salt comprises salts of two or more fatty acids selected from the group consisting of $C_{8-22}$ saturated fatty acids and unsaturated fatty acids.

* * * * *